(12) United States Patent
Frangioni et al.

(10) Patent No.: US 7,181,266 B2
(45) Date of Patent: *Feb. 20, 2007

(54) MATERIALS AND METHODS FOR NEAR-INFRARED AND INFRARED LYMPH NODE MAPPING

(75) Inventors: John V. Frangioni, Wayland, MA (US); Moungi G. Bawendi, Cambridge, MA (US); Sungjee Kim, Pasadena, CA (US); Yong Taik Lim, Duckjin-Gu (KR)

(73) Assignees: Massachusetts Institute of Technology, Cambridge, MA (US); Beth Isreal Deaconess Medical Center, Inc., Boston, MA (US)

( * ) Notice: Subject to any disclaimer, the term of this patent is extended or adjusted under 35 U.S.C. 154(b) by 239 days.

This patent is subject to a terminal disclaimer.

(21) Appl. No.: 10/772,425

(22) Filed: Feb. 6, 2004

(65) Prior Publication Data

US 2005/0020923 A1    Jan. 27, 2005

Related U.S. Application Data

(60) Provisional application No. 60/451,246, filed on Mar. 4, 2003.

(51) Int. Cl.
*A61B 5/00* (2006.01)
*A61N 5/06* (2006.01)
(52) U.S. Cl. .................. 600/476; 424/9.3; 424/490; 600/3; 977/813; 977/881; 977/904; 977/949; 977/954

(58) Field of Classification Search .............. 424/1.29, 424/1.41, 9.3, 490; 600/431, 310, 317, 476; 977/904, 927, 949, 954, 813, 881
See application file for complete search history.

(56) References Cited

U.S. PATENT DOCUMENTS

| 5,101,827 | A |   | 4/1992  | Goldenberg        |
|-----------|---|---|---------|-------------------|
| 5,262,357 | A |   | 11/1993 | Alivisatos et al. |
| 5,496,536 | A | * | 3/1996  | Wolf ........... 424/9.322 |
| 5,505,928 | A |   | 4/1996  | Alivisatos et al. |
| 5,525,377 | A |   | 6/1996  | Gallagher et al.  |
| 5,537,000 | A |   | 7/1996  | Alivisatos et al. |
| 5,585,640 | A |   | 12/1996 | Huston et al.     |
| 5,674,698 | A |   | 10/1997 | Zarling et al.    |
| 5,677,545 | A |   | 10/1997 | Shi et al.        |
| 5,751,018 | A |   | 5/1998  | Alivisatos et al. |
| 5,985,173 | A |   | 11/1999 | Grey et al.       |

(Continued)

FOREIGN PATENT DOCUMENTS

WO    WO 98/04740    2/1998

(Continued)

OTHER PUBLICATIONS

Gao et al., "In Vivo cancer targeting and imaging with semiconductor quantum dots", Nature Biotechnology, vol. 22, No. 8, Aug. 2004, 969-976.*

(Continued)

*Primary Examiner*—H. Thi Le
(74) *Attorney, Agent, or Firm*—Steptoe & Johnson LLP

(57) ABSTRACT

A lymphatic system can be imaged with emissive semiconductor nanocrystals, for example, in the near infrared.

24 Claims, 10 Drawing Sheets

U.S. PATENT DOCUMENTS

| | | | |
|---|---|---|---|
| 5,985,353 A | 11/1999 | Lawton et al. | |
| 5,990,479 A | 11/1999 | Weiss et al. | |
| 6,054,495 A | 4/2000 | Markowitz et al. | |
| 6,114,038 A | 9/2000 | Castro et al. | |
| 6,139,585 A | 10/2000 | Li | |
| 6,159,445 A * | 12/2000 | Klaveness et al. | 424/9.6 |
| 6,165,440 A * | 12/2000 | Esenaliev | 424/1.11 |
| 6,167,297 A * | 12/2000 | Benaron | 600/431 |
| 6,207,229 B1 | 3/2001 | Bawendi et al. | |
| 6,207,392 B1 * | 3/2001 | Weiss et al. | 435/7.1 |
| 6,251,303 B1 | 6/2001 | Bawendi et al. | |
| 6,306,610 B1 | 10/2001 | Bawendi et al. | |
| 6,319,426 B1 | 11/2001 | Bawendi et al. | |
| 6,326,144 B1 | 12/2001 | Bawendi et al. | |
| 6,337,117 B1 | 1/2002 | Maenosono et al. | |
| 6,379,635 B2 | 4/2002 | O'Brien et al. | |
| 6,410,255 B1 | 6/2002 | Pollok et al. | |
| 6,444,143 B2 | 9/2002 | Bawendi et al. | |
| 6,444,192 B1 * | 9/2002 | Mattrey | 424/9.52 |
| 6,447,698 B1 | 9/2002 | Ihara et al. | |
| 6,501,091 B1 | 12/2002 | Bawendi et al. | |
| 6,530,944 B2 * | 3/2003 | West et al. | 607/88 |
| 6,548,168 B1 | 4/2003 | Mulvaney et al. | |
| 6,548,171 B1 | 4/2003 | Barbera-Guillem et al. | |
| 6,633,370 B2 | 10/2003 | Lawandy | |
| 6,636,755 B2 * | 10/2003 | Toida | 600/407 |
| 6,804,549 B2 * | 10/2004 | Hayashi | 604/431 |
| 6,815,064 B2 * | 11/2004 | Treadway et al. | 428/403 |
| 6,819,692 B2 | 11/2004 | Klimov et al. | |
| 6,861,155 B2 * | 3/2005 | Bawendi et al. | 428/549 |
| 2002/0066401 A1 | 6/2002 | Peng et al. | |
| 2003/0017264 A1 | 1/2003 | Treadway et al. | |
| 2003/0042850 A1 | 3/2003 | Bertram et al. | |
| 2003/0113709 A1 * | 6/2003 | Alivisatos et al. | 435/4 |
| 2003/0206859 A1 * | 11/2003 | Chen et al. | 424/9.1 |
| 2004/0036085 A1 * | 2/2004 | Sato et al. | 257/200 |
| 2005/0020922 A1 * | 1/2005 | Frangioni et al. | 600/473 |
| 2005/0113697 A1 * | 5/2005 | Ottoboni et al. | 600/458 |
| 2005/0175540 A1 * | 8/2005 | Oraevsky et al. | 424/9.5 |
| 2005/0220714 A1 * | 10/2005 | Kauzlarich et al. | 424/9.32 |

FOREIGN PATENT DOCUMENTS

| | | |
|---|---|---|
| WO | WO 98/33070 | 7/1998 |
| WO | WO 00/27365 | 5/2000 |
| WO | WO 00/27436 | 5/2000 |
| WO | WO 00/28088 | 5/2000 |
| WO | WO 00/28089 | 5/2000 |

OTHER PUBLICATIONS

Akerman et al., *Proc. Natl. Acad. Sci. USA* 99:12617-12621 (2002).

Alivisatos, "Perspectives on the Physical Chemistry of Semiconductor Nanocrystals" *J. Phys. Chem.* 1996(100):13226-13239, 1996.

Bruchez et al., "Semiconductor Nanocrystals as Fluorescent Biological Labels," *Science*, 281:2013-2016, Sep. 25, 1998.

Dabbousi, et al., "(CdSe)ZnS core-shell quantum dots: synthesis and characterization of a size series of highly luminescent nanocrystallites" *J. of Phys. Chem. B* 101(46):9463-9475, Nov. 13, 1997.

Gao et al., "Strongly Photoluminescent CdTe Nanocrystals by Proper Surface Modification," *J. Phys. Chem.*, 102:8360-8363, 1998.

Han M. et al., "Quantum-dot-tagged microbeads for multiplexed optical coding of biomolecules," *Nature Biotech.* 19:631-635.

Mikulec et al., "Fluorescent semiconductor nanocrystallites derivatized with biomolecules" *Amer. Chem.. Soc. Nat'l Meeting*, Boston, MA, Aug. 24, 1998.

Spanhel et al., "Photochemistry of Colloidal Semiconductors. Surface Modification and Stability of Strong Luminescing CdS Particles" *J. Am. Chem. Soc.* 109(19):5649-5655, 1987.

Wu et al., "Immunofluorescent labeling of cancer marker Her2 and other cellular targets with semiconductor quantum dots," *Nature Biotechnology* 21:1, 41-46, Jan. 2003.

Ekimov, A.I. et al., "Growth and optical properties of semiconductor nanocrystals in a glass matrix," *Journal of Luminescence* 70 (1996) 1-20.

Ekimov, A.I. et al., "Effects of Resonance on Low-Frequency Raman Scattering From Semiconductor Nanocrystals," *Radiation Effects and Defects in Solids*, 1995, vol. 137, pp. 45-50.

Ekimov, A.I. et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Ekimov, A.I. et al., "Optics of Zero Dimensional Semiconductor Systems, *Acta Physica Polonica A*," vol. 79 (1991), No. 1. pp. 5-14.

Ekimov, A.I. et al., "Time-Resolved Luminescence of CdSe Microcrystals," *Solid State Communications*, vol. 74, No. 7, pp. 555-557, 1990.

Ekimov, A.I. et al., "Quantum-Size Stark Effect in Semiconductor Microcrystals,".

Ekimov, A.I. et al., "Donor-like Exciton in Zero-Dimension Semiconductor Structures," *Solid State Communications*, vol. 69, No. 5, pp. 565-568, 1989.

Ekimov, A.I. et al., "Nonlinear optical properties of semiconductor microcrystals," *JETP Lett.*, vol. 46, No. 10, Nov. 25, 1987 pp. 435-439.

Ekimov, A.I. et al., "Quantum Size Effect in Semiconductor Microcrystals," *Solid State Communications*, vol. 56, No. 11, pp. 921-924, 1985.

Ekimov, A.I. et al., "Size quantization of the electron energy spectrum in a microscopic semiconductor crystal," *JETP Lett.*, vol. 40, No. 8, Oct. 25, 1984, pp. 1136-1139.

Ekimov, A.I. et al., "Quantum size effect in the optical spectra of semiconductor microcrystals," *Sov. Phys. Semicond.* 16(7), Jul. 1982, pp. 775-778.

Ekimov, A.I. et al., "Quantum size effect in three-dimensional microscopic semiconductor crystals," *JETP Lett*, vol. 34, No. 6, Sep. 20, 1981, pp. 345-349.

* cited by examiner

A.

B.

C.

D.

A.

A.

Color Video | NIR Autofluorescence | 5 min Post-Injection

B.

Color Video | 5 min Post-Injection

MATERIALS AND METHODS FOR NEAR-INFRARED AND INFRARED LYMPH NODE MAPPING

CLAIM OF PRIORITY

This application claims priority under 35 U.S.C. § 119(e) to U.S. Patent Application Ser. No. 60/451,246, filed on Mar. 4, 2003, the entire contents of which are hereby incorporated by reference.

FEDERALLY SPONSORED RESEARCH OR DEVELOPMENT

This invention was made with government support under Grant No. 1-R21-EB00673-01, awarded by NIH, and Grant No. DMR-0213282, awarded by NSF. The government has certain rights in this invention.

TECHNICAL FIELD

The invention relates to lymph node mapping.

BACKGROUND

Semiconductor nanocrystals (QDs) having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases. Semiconductor nanocrystals can have a narrow fluorescence band whose emission wavelength is tunable with the size and material of the nanocrystals.

SUMMARY

In general, emissive semiconductor nanocrystals can be used to map the lymphatic system. Mapping of the lymphatic system can include real-time mapping of sentinel lymph nodes (SLN). In conjunction with the intraoperative NIR fluorescence imaging system, near infrared (NIR) and infrared (IR) emission from semiconductor nanocrystals can be used to provide a surgeon with light-based, sensitive, specific, and real-time mapping of sentinel lymph nodes. The emissive semiconductor nanocrystals, in combination with an intraoperative NIR emission imaging system can provide SLN mapping for all types of human solid cancers, especially melanoma.

Traditionally, intraoperative sentinel lymph node (SLN) mapping for melanoma and breast cancer is performed using a combination of radioactive tracers and blue dyes. Radioactive tracers, such as Technetium-99m sulfur colloid, emits mid-energy (140 keV) gamma rays within the body. Isosulfan blue, a blue dye (trade name Lymphazurin™), is used at a concentration of about 17 mM to locate the SLN. The blue dye requires surgical exploration to find the lymph node. Advantageously, emissive semiconductor nanocrystals can be monitored through the skin to identify the sentinel node, avoiding or minimizing surgical exploration. In addition, this light-based approach can replace or supplement radioactivity and blue dye tracing, can permit imaging of lymph node flow in real-time, not just approximate positions given by radioactive tracers, and, because NIR and IR light is used, can permit even deep lymph nodes to be mapped. The nanocrystals are excited by light, and emit light, thereby replacing the need to produce images using X-ray technology.

In one aspect, a lymphatic imaging composition includes a particle including a semiconductor nanocrystal having an outer layer bonded to the nanocrystal, the particle having a diameter between 10 nm and 20 nm.

In another aspect, a method of imaging a lymphatic system of an animal includes introducing a composition subcutaneously in the mammal, the composition including a particle including a semiconductor nanocrystal, and detecting emission from the particle. The composition can be introduced proximate to a tumor site in the animal. Detecting emission can include generating an image in the near-infrared or infrared wavelength region. The method can include generating a composite image including a real-time image of an area surrounding the injection site and the image in the near-infrared or infrared wavelength region. The particle can have a diameter of between 10 nm and 20 nm. The method can include exposing the animal to white light. Detecting emission can include monitoring a site of the mammal that is protected by skin.

In another aspect, an imaging system includes a white light source capable of being directed at a portion of a patient, an imaging composition including a particle including a semiconductor nanocrystal, and a detector configured to monitor emission from the particle in the patient.

The outer layer can include a polydentate ligand. The particle can emit light having a wavelength greater than 800 nm. The nanocrystal can include a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating.

Other features, objects, and advantages will be apparent from the description and drawings, and from the claims.

DETAILED DESCRIPTION

It is well known from the literature that particle size is a key determinant for SLN mapping. The radiopharmaceuticals which have been most widely used in identifying SLN drainage patterns in patients with cutaneous melanoma and breast cancer include: Technetium-99m sulfur colloid, Technetium-99m antimony sulfide, Technetium-99m nanocolloid, and Technetium-99m human serum albumin. The major differences between these agents are the size of the colloid particles or albumin molecules. Since the rate of colloid transport through lymphatics is a function of colloid particle size, this is a critical factor for performance of lymph scintigraphy. The largest particles (>200 nm) simply remain at the injection site, and the smallest (<5 nm) rapidly partition into the bloodstream. Particles between 5 to 10 nm in size enter the lymphatics rapidly, but spread to numerous nodes.

Sentinel lymph node localization depends on a small fraction of the injected isotope dose (perhaps 1%) migrating consistently to relatively few regional nodes. The optimal particle size can be between 10 and 50 nm. Both Technetium-99m antimony sulfide colloid and nanocolloid of albumin labeled with Technetium-99m, have excellent retention in SLNs, and have been used specifically for lymphoscintigraphy in humans. Antimony sulfide colloid has particles of relatively uniform size, most with diameters in the 10–15 nm range. Antimony sulfide colloid particles are an ideal size to pass freely into the lymphatic capillaries via the 10–25 nm clefts between overlapping cells and the intercellular gaps, which can be considerably larger than this. These particles migrate rapidly through the lymphatic channels to the SLN, yet are retained in the SLN for up to 24 hours. Patent blue vital dye spreads rapidly to the SLN, but also passes freely into the bloodstream, giving a bluish tinge to skin and urine for several days. In fact, during surgery and the recovery phase, patients have exceptionally pale, blue-green colored skin.

Figure 1A:
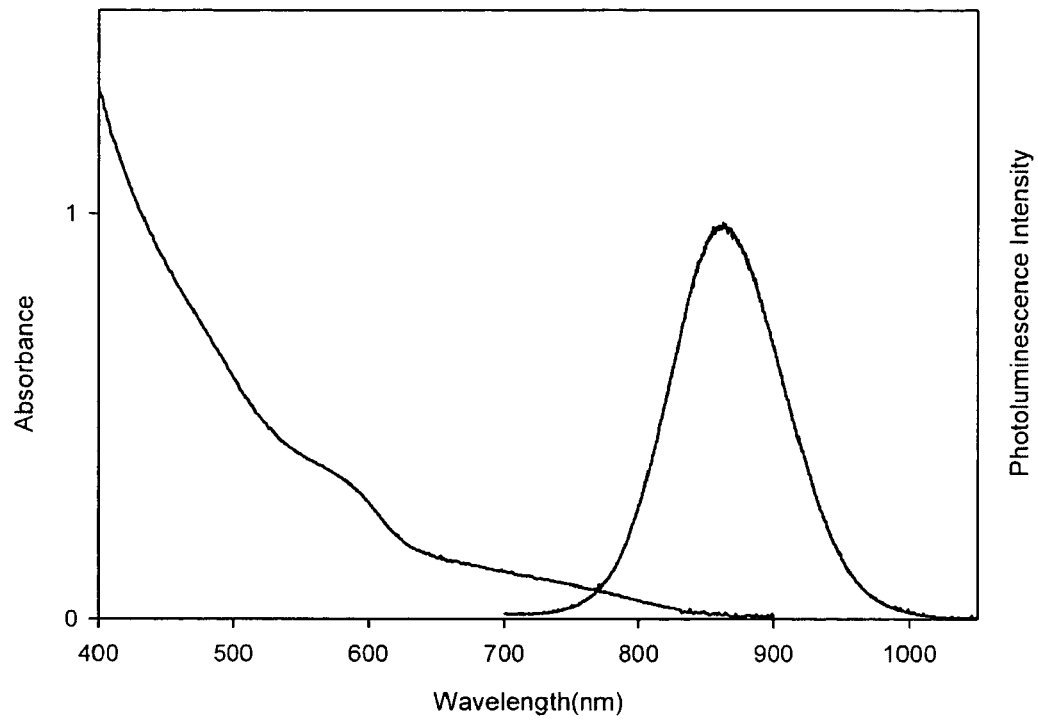
FIG. 1A is a graph depicting measurement of NIR nanocrystal hydrodynamic diameter.

Based on theoretical modeling described below, the two best emission wavelengths for in vivo imaging with nanocrystals are 720–900 nm (NIR nanocrystals) and 1250–400 nm (IR nanocrystals). To create NIR nanocrystals of 860 nm peak emission wavelength, a type II heterostructure can be used. The core can be CdTe and the shell can be CdSe. The color of the fluorescence of these type II nanocrystals is determined by the band offsets between the core and the shell. Tuning the core size and shell thickness allows for tunable emission in the 800–900 nm range. The emissive semiconductor nanocrystals approximately 15–20 nm in hydrodynamic diameter, and have proven by gel filtration (see FIG. 1A) that they are, indeed, of this size. In FIG. 1A, gel filtration on Sephacryl S-300 resin was used in conjunction with MW standards (shown) to determine the effective hydrodynamic diameter of NIR nanocrystals. Diameter of the nanocrystals was approximately 15–20 nm, and the width of the peak (indicative of size variation in the preparation) is close to that of albumin. Other applications of semiconductor nanocrystals for imaging are described in co-pending application filed Mar. 4, 2003, entitled, "Materials and methods for near-infrared and infrared intravascular imaging," U.S. Ser. No. 60/451,247, which is incorporated by reference in its entirety.

One surgical procedure during which radiation is used routinely is sentinel lymph node (SLN) mapping and biopsy. The underlying hypothesis of SLN mapping is that the first lymph node to receive lymphatic drainage from a tumor site will show tumor if there has been lymphatic spread. SLNs can be identified using radio-guided lymphatic mapping and/or by visualization of the nodes with vital blue dyes. Histopathological evaluation of SLNs provides accurate staging of cancer, and can guide regional and systematic treatment. Importantly, for breast cancer, axillary node dissection and its associated morbidity can be avoided in patients whom the SLN is negative histologically. Another benefit of SLN mapping is that it affords excellent regional control in the patient with palpable tumor-containing nodes. This light-based approach can replace radioactivity and blue dyes, can permits imaging of lymph node flow in real-time, not just approximate positions given by radioactive tracers, and can permits even deep lymph nodes to be mapped by monitoring emitted NIR or IR wavelength ranges.

Fluorescent semiconductor nanocrystals are excellent contrast agents for biomedical assays and imaging. A unique property of semiconductor nanocrystals is that their absorbance increases with increasing separation between excitation and emission wavelengths. Much of the enthusiasm for using semiconductor nanocrystals in vivo stems from this property, since photon yield should be proportional to the integral of the broadband absorption. Tissue scatter and absorbance can sometimes offset increasing semiconductor nanocrystal absorption at bluer wavelengths, and counteract this potential advantage. By using a previously validated mathematical model, the effects of tissue absorbance, tissue scatter, wavelength dependence of the scatter, water to hemoglobin ratio, and tissue thickness on semiconductor nanocrystal performance were explored. When embedded in biological fluids and tissues, semiconductor nanocrystal excitation wavelengths can be quite constrained, and that excitation and emission wavelengths should be selected carefully based on the particular application. Near-infrared semiconductor nanocrystals optimized for imaging systems with white light excitation and a silicon CCD camera were produced and used to image the sentinel lymph node in real time. Emissive fluorescent semiconductor nanocrystal contrast agents optimized for specific biomedical applications.

Semiconductor nanocrystals are inorganic fluorophores that are currently being investigated for use as luminescent biological probes due to their nanometer dimensions and unique optical properties. Compared to conventional fluorophores and organic dyes, semiconductor nanocrystals have a number of attractive characteristics including high absorption cross-section, broadband absorption that increases at bluer wavelengths, relatively narrow and symmetric luminescence bands, simultaneous excitation of semiconductor nanocrystals with different emission wavelengths using a single excitation wavelength, and potentially high resistance to photo-degradation. Although the synthesis of semiconductor nanocrystals is performed in organic solvents, various surface chemistries can impart aqueous solubility and permit conjugation to biomolecules such as proteins, oligonucleotides, antibodies, and small molecule ligands. Such "targeted" semiconductor nanocrystals have been reported as contrast agents for nucleic acid hybridization, cellular imaging, immunoassays, and recently, tissue-specific homing in vivo. See, for example, Bruchez et al., *Science* 281:2013–2016 (1998); Chan and Nie, *Science* 281:2016–2018 (1998); Mattoussi et al., *J. Am. Chem. Soc.*

122:12142–12150 (2000); Klarreich, *Nature* 413:450–452 (2001); Chan et al., *Curr Opin Biotechnol* 13:40–46 (2002); Wu et al., "Immunofluorescent labeling of cancer marker Her2 and other cellular targets with semiconductor quantum dots," *Nature Biotechnol.*, published online Dec. 2, 2002 doi: 10.1038/nbt764; Dubertret et al., *Science* 298:1759–1762 (2002); Pathak et al., *J. Am. Chem. Soc.* 123:4103–4104 (2001); Gerion et al., *J. Am. Chem. Soc.* 124:7070–7074 (2002); Goldman et al., *J. Am. Chem. Soc.* 124:6378–6382 (2002); Goldman et al., *Anal. Chem.* 74:841–847 (2002); Rosenthal et al., *J. of the Am. Chem. Soc.* 124:4586–4594 (2002); Akerman et al., *Proc. Natl. Acad. Sci. USA* 99:12617–12621 (2002); and Jaiswal et al., "Long-term multiple color imaging of live cells using quantum dot bioconjugates," *Nature Biotechnol.*, published online Dec. 2, 2002 doi: 10.1038/nbt767, each of which is incorporated by reference in its entirety.

Another potential application of semiconductor nanocrystals is as fluorescent contrast agents for biomedical imaging. However, in vivo applications, and especially reflectance fluorescence imaging (the impetus for this study), require deep photon penetration into and out of tissue. In living tissue, total photon attenuation is the sum of attenuation due to absorbance and scatter. Scatter describes the deviation of a photon from the parallel axis of its path, and can occur when the tissue inhomogeneity is small relative to wavelength (Rayleigh-type scatter), or roughly on the order of wavelength (Mie-type scatter). For inhomogeneities at least ten times less than the wavelength, Rayleigh-type scatter is proportional to the reciprocal $4^{th}$ power of wavelength. In living tissue, photon scatter is the result of multiple scattering events, and in general terms can be considered either dependent on wavelength or independent of wavelength. For example, in rat skin, scatter is proportional to $\lambda^{-2.8}$, suggesting strong wavelength-dependence, however, in post-menopausal human breast, scatter is proportional to $\lambda^{-0.6}$, suggesting weak wavelength-dependence. See, for example, Zaheer et al., *Nature Biotechnol.* 19:1148–1154 (2001); Nakayama et al., "Functional near-infrared fluorescence imaging for cardiac surgery and targeted gene therapy," *Molecular Imaging* (2002); Cheong et al., *IEEE J. Quantum Electronics* 26:2166–2195 (1990); and Cerussi et al., *Acad. Radiol.* 8:211–218 (2001), each of which is incorporated by reference in its entirety.

Given the relatively low absorbance and scatter of living tissue in the near-infrared (NIR; 700 nm to 1000 nm) region of the spectrum, considerable attention has focused on NIR fluorescence contrast agents. For example, conventional NIR fluorophores with peak emission between 700 nm and 800 nm have been used for in vivo imaging of protease activity, somatostatin receptors, sites of hydroxylapatite deposition, and myocardial vascularity, to name a few. To date, however, a systematic analysis of how tissue optical properties might affect semiconductor nanocrystal performance in vivo, and whether infrared (IR), rather than NIR, wavelengths could potentially improve overall photon yield, has not been presented. A previously described mathematical model was used to predict how various tissue characteristics will affect semiconductor nanocrystal performance in vivo, and this model was used to select optimal semiconductor nanocrystal excitation and emission wavelengths for various imaging applications. Based on these results, a particular NIR semiconductor nanocrystal was synthesized and used in real-time in vivo imaging. See, for example, Zaheer et al., *Nature Biotechnol.* 19:1148–1154 (2001); Nakayama et al., "Functional near-infrared fluorescence imaging for cardiac surgery and targeted gene therapy," *Molecular Imaging* (2002); Weissleder, *Nature Biotechnol.* 19:316–7 (2001); Weissleder et al., *Nature Biotechnol.* 17:375–378 (1999); Becker et al., *Nature Biotechnol.* 19:327–31 (2001); and Bugaj et al., *J. Biomed. Opt.* 6:122–33 (2001); Gardner et al., *Lasers Surg. Med.* 18:129–38 (1996), each of which is incorporated by reference in its entirety.

Nanocrystal cores can be prepared by the pyrolysis of organometallic precursors in hot coordinating agents. See, for example, Murray, C. B., et al., *J. Am. Chem. Soc.* 1993, 115, 8706, and Mikulec, F., Ph.D. Thesis, MIT, Cambridge, 1999, each of which is incorporated by reference in its entirety. Growth of shell layers on the bare nanocrystal cores can be carried out by simple modifications of conventional overcoating procedures. See, for example, Peng, X., et al., *J. Am. Chem. Soc.* 1997, 119, 7019, Dabbousi, B. O., et al., *J. Phys. Chem. B* 1997, 101, 9463, and Cao, Y. W. and Banin U. *Angew. Chem. Int. Edit.* 1999, 38, 3692, each of which is incorporated by reference in its entirety.

A coordinating agent can help control the growth of the nanocrystal. The coordinating agent is a compound having a donor lone pair that, for example, has a lone electron pair available to coordinate to a surface of the growing nanocrystal. Solvent coordination can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

The outer surface of the nanocrystal can include a layer of compounds derived from the coordinating agent used during the growth process. The surface can be modified by repeated exposure to an excess of a competing coordinating group to form an overlayer. For example, a dispersion of the capped nanocrystal can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Monodentate alkyl phosphines (and phosphine oxides, the term phosphine below will refer to both) can passivate nanocrystals efficiently. When nanocrystals with conventional monodentate ligands are diluted or embedded in a non-passivating environment (i.e. one where no excess ligands are present), they tend to lose their high luminescence and their initial chemical inertness. Typical are an abrupt decay of luminescence, aggregation, and/or phase separation. In order to overcome these limitations, polydentate ligands can be used, such as a family of polydentate oligomerized phosphine ligands. The polydentate ligands show a high affinity between ligand and nanocrystal nanocrystal surface. In other words, they are stronger ligands, as is expected from the chelate effect of their polydentate characteristics. Oligomeric phosphines have more than one binding site to the nanocrystal surface, which ensures their high affinity to the nanocrystal surface. See, for example, for example, U.S. Ser. No. 10/641,292, filed Aug. 15, 2003, and U.S. Ser. No. 60/403,367, filed Aug. 15, 2002, each of which is incorporated by reference in its entirety. The oligomeric phosphine can be formed from a monomeric, polyfunctional phosphine, such as, for example, trishydroxypropylphosphine, and a polyfunctional oligomerization reagent, such as, for example, a diisocyanate. The oligomeric phosphine can be contacted with an isocyanate of formula R'-L-NCO, wherein L is $C_2$–$C_{24}$ alkylene, and R' has the formula

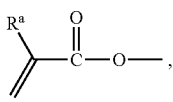

R' has the formula

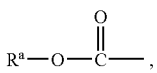

or R' is hydrogen, wherein $R^a$ is hydrogen or $C_1$–$C_4$ alkyl.

Bioconjugation to the outer surface of nanocrystals can be accomplished. For example, nanocrystals with oligomeric phosphine with carboxylic acid can be coupled to amine-derivatized biomolecules via carbodiimide couplings using EDC(1-ethyl-3-(3-dimethylaminopropyl)carbodiimide hydrochloride). The general coupling reaction is described, for example, in Hermanson, G. T. *Bioconjugate Techniques* 1996 Academic Press, which is incorporated by reference in its entirety. Elecrostatic interactions can be also used as thiol-based ligands with carboxylic acid. See, for example, Mattoussi, H., et al., J. Am. Chem. Soc. 2000, 122, 12142, and Goldman, E. R., et al., 2002 J. Am. Chem. Soc 124, 6378, each of which is incorporated by reference in its entirety. Nanocrystals with small oligomeric phosphine can be coupled to many biomolecules using carbonyldiimidazole or epichlorohydrin. See, for example, Pathak S., et al., 2001 *J. Am. Chem. Soc* 123, 4103, and Hermanson, G. T. *Bioconjugate Techniques* 1996 Academic Press, each of which is incorporated by reference in its entirety.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The semiconductor forming the core of the nanocrystal can include Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The quantum efficiency of emission from nanocrystals having a core of a first semiconductor material be enhanced by applying an overcoating of a second semiconductor material such that the conduction band of the second semiconductor material is of higher energy than that of the first semiconductor material, and the valence band of the second semiconductor material is of lower energy than that of the first semiconductor material. As a result, carriers, i.e., electrons and holes, are confined in the core of the nanocrystal. The core can have an overcoating on a surface of the core. The overcoating can be a semiconductor material having a composition different from the composition of the core, and can have a band gap greater than the band gap of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. Semiconductor nanocrystals can have emission quantum efficiencies of greater than 2%, 5%, 10%, 20%, 40%, 60%, 70%, or 80%.

Methods of preparing semiconductor nanocrystals include pyrolysis of organometallic reagents, such as dimethyl cadmium, injected into a hot, coordinating agent. This permits discrete nucleation and results in the controlled growth of macroscopic quantities of nanocrystals. Preparation and manipulation of nanocrystals are described, for example, in U.S. application Ser. No. 08/969,302, incorporated herein by reference in its entirety. The method of manufacturing a nanocrystal is a colloidal growth process and can produce a monodisperse particle population. Colloidal growth occurs by rapidly injecting an M donor and an X donor into a hot coordinating agent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or X donor, the growth period can be shortened.

An overcoating process is described, for example, in U.S. application Ser. No. 08/969,302, incorporated herein by reference in its entirety. By adjusting the temperature of the reaction mixture during overcoating and monitoring the absorption spectrum of the core, over coated materials having high emission quantum efficiencies and narrow size distributions can be obtained. Alternatively, an overcoating can be formed by exposing a core nanocrystal having a first composition and first average diameter to a population of nanocrystals having a second composition and a second average diameter smaller than the first average diameter.

The M donor can be an inorganic compound, an organometallic compound, or elemental metal. M is cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis (silyl) chalcogenide, dioxygen, an ammonium salt, or a tris(silyl) pnictide. Suitable X donors include dioxygen, bis(trimethylsilyl)selenide (($TMS)_2Se$), trialkyl phosphine selenides such as (tri-n-octylphosphine)selenide (TOPSe) or (tri-n-butylphosphine)selenide (TBPSe), trialkyl phosphine tellurides such as (tri-n-octylphosphine)telluride (TOPTe) or hexapropylphosphorustriamide telluride (HPPTTe), bis(trimethylsilyl)telluride (($TMS)_2Te$), bis(trimethylsilyl)sulfide (($TMS)_2S$), a trialkyl phosphine sulfide such as (tri-n-octylphosphine)sulfide (TOPS), an ammonium salt such as an ammonium halide (e.g., $NH_4Cl$), tris(trimethylsilyl)phosphide (($TMS)_3P$), tris(trimethylsilyl)arsenide (($TMS)_3As$), or tris(trimethylsilyl)antimonide (($TMS)_3Sb$). In certain embodiments, the M donor and the X donor can be moieties within the same molecule.

The semiconductor nanocrystal can emit light in the near infrared (NIR) or infrared (IR) wavelength regions when excited with incident radiation. An example of a semiconductor nanocrystal that emits light in the near infrared or infrared wavelength regions is a semiconductor nanocrystal heterostructure, which has a core of a first semiconductor material surrounded by an overcoating of a second semiconductor material. The first semiconductor material and second semiconductor material are selected so that, upon excitation, one carrier is substantially confined to the core and the other carrier is substantially confined to the overcoating. See, for example, U.S. Ser. No. 10/641,292, filed Aug. 15, 2003, and U.S. Ser. No. 60/402,726, filed Aug. 13, 2002, each of which is incorporated by reference in its entirety.

In one example, the conduction band of the first semiconductor material is at higher energy than the conduction band of the second semiconductor material and the valence band of the first semiconductor material is at higher energy than the valence band of the second semiconductor material. In another example, the conduction band of the first semiconductor material is at lower energy than the conduction band of the second semiconductor material and the valence band of the first semiconductor material is at lower energy than the valence band of the second semiconductor material. These band alignments make spatial separation of the hole and the electron energetically favorable upon excitation. These structures are type II heterostructures. In contrast, the configurations in which the conduction band of the second semiconductor material is of higher energy than that of the first semiconductor material, and the valence band of the second semiconductor material is of lower energy than that of the first semiconductor material are type I heterostructures. The language of type I and type II is borrowed from the quantum well literature where such structures have been extensively studied.

Nanocrystals having type II heterostructures have advantageous properties that result of the spatial separation of carriers. In some nanocrystals having type II heterostructures the effective band gap, as measured by the difference in the energy of emission and energy of the lowest absorption features, can be to the red of either of the two semiconductors making up the structure. By selecting particular first semiconductor materials and second semiconductor materials, and core diameters and overcoating thicknesses, nanocrystals having type II heterostructures can have emission wavelengths previously unavailable with the semiconductor of the nanocrystal core in previous structures. In addition, the separation of charges in the lowest excited states of nanocrystals having type II heterostructures can make these materials more efficient in photovoltaic or photoconduction devices where the nanocrystals are chromophores and one of the carriers needs to be transported away from the excitation site prior to recombination.

Advantageously, a wide variety of nanocrystals having type II heterostructures can be prepared using colloidal synthesis. Colloidal synthesis allows nanocrystals to be prepared with controllable dispersibility imparted from coordinating agents, such as ligands, and are prepared in the absence of wetting layers commonly employed in nanocrystals having type II heterostructures prepared by molecular beam epitaxy.

The overcoating can be a semiconductor material having a composition different from the composition of the core which is selected to provide a type II heterostructure. The overcoat of a semiconductor material on a surface of the nanocrystal can include a Group II-VI compounds, Group II-V compounds, Group III-VI compounds, Group III-V compounds, Group IV-VI compounds, Group 1-III-VI compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. For example, ZnS, ZnSe or CdS overcoatings can be grown on CdSe or CdTe nanocrystals.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter, a population having an average nanocrystal diameter of less than 150 Å can be obtained. A population of nanocrystals can have an average diameter of 15 Å to 125 Å.

The particle size distribution can be further refined by size selective precipitation with a poor solvent for the nanocrystals, such as methanol/butanol as described in U.S. application Ser. No. 08/969,302, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

Transmission electron microscopy (TEM) can provide information about the size, shape, and distribution of the nanocrystal population. Powder x-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from x-ray diffraction data using, for example, the Scherrer equation. It also can be estimated from the UV/Vis absorption spectrum.

The nanocrystal can be incorporated into composition, such as an injectable preparation that can include an acceptable diluent, or a slow release matrix in which the nanocrystal is imbedded. The composition can be provided in a container, pack, or dispenser together with instructions for administration. The composition can be formulated in accordance with their intended route of administration. Acceptable routes include oral or parenteral routes (e.g., intravenous, intradermal, transdermal (e.g., subcutaneous or topical), or transmucosal (i.e., across a membrane that lines the respiratory or anogenital tract). The compositions can be formulated as a solution or suspension and, thus, can include a sterile diluent (e.g., water, saline solution, a fixed oil, polyethylene glycol, glycerine, propylene glycol or another synthetic solvent); an antimicrobial agent (e.g., benzyl alcohol or methyl parabens; chlorobutanol, phenol, ascorbic acid, thimerosal, and the like); an antioxidant (e.g., ascorbic acid or sodium bisulfite); a chelating agent (e.g., ethylenediaminetetraacetic acid); or a buffer (e.g., an acetate-, citrate-, or phosphate-based buffer). When necessary, the pH of the solution or suspension can be adjusted with an acid (e.g., hydrochloric acid) or a base (e.g., sodium hydroxide). Proper fluidity (which can ease passage through a needle) can be maintained by a coating such as lecithin, by maintaining the required particle size (in the case of a dispersion), or by the use of surfactants. The body can be an animal (e.g., a rabbit, mouse, guinea pig, rat, horse, cow, pig, dog, cat or human).

Materials and Methods

Animals. Animals were used in accordance with an approved institutional protocol. Male Sprague-Dawley rats were from Charles River Laboratories (Wilmington, Mass.). Hairless athymic nu/nu mice were from Taconic (Germantown, N.Y.). Rats and mice were anesthetized with 65 mg/kg and 50 mg/kg intraperitoneal pentobarbital, respectively.

Reagents. Sterile Intralipid™ (20%) was purchased from Baxter (Deerfield, Ill.). Water was purified on a Milli-Q system (Millipore, Bedford, Mass.). Olive oil was from Filippo Berio (Viareggio, Italy). Oxyhemoglobin (OxyHb) was prepared from normal human donors as described in Drabkin, *J. Biol. Chem.* 164:703–723 (1946), which is incorporated by reference in its entirety. Deoxyhemoglobin (DeoxyHb) was prepared by treatment of OxyHb with 1% sodium dithionite (Sigma, St. Louis, Mo.). Albumin, Cohn Fraction V was also from Sigma. All solutions except Intralipid were filtered through 0.2 μm filters (Millipore) prior to use to eliminate scatter. Trioctylphosphine oxide (TOPO), selenium shot, and tellurium shot were from Alfa Aesar (Ward Hill, Mass.). Trioctylphosphine (TOP) was from Fluka (St. Louis, Mo.). Hexadecylamine (HDA) was from Aldrich (St. Louis, Mo.). All other reagents were purchased from Fisher Scientific (Hanover Park, Ill.).

Figure 1B:
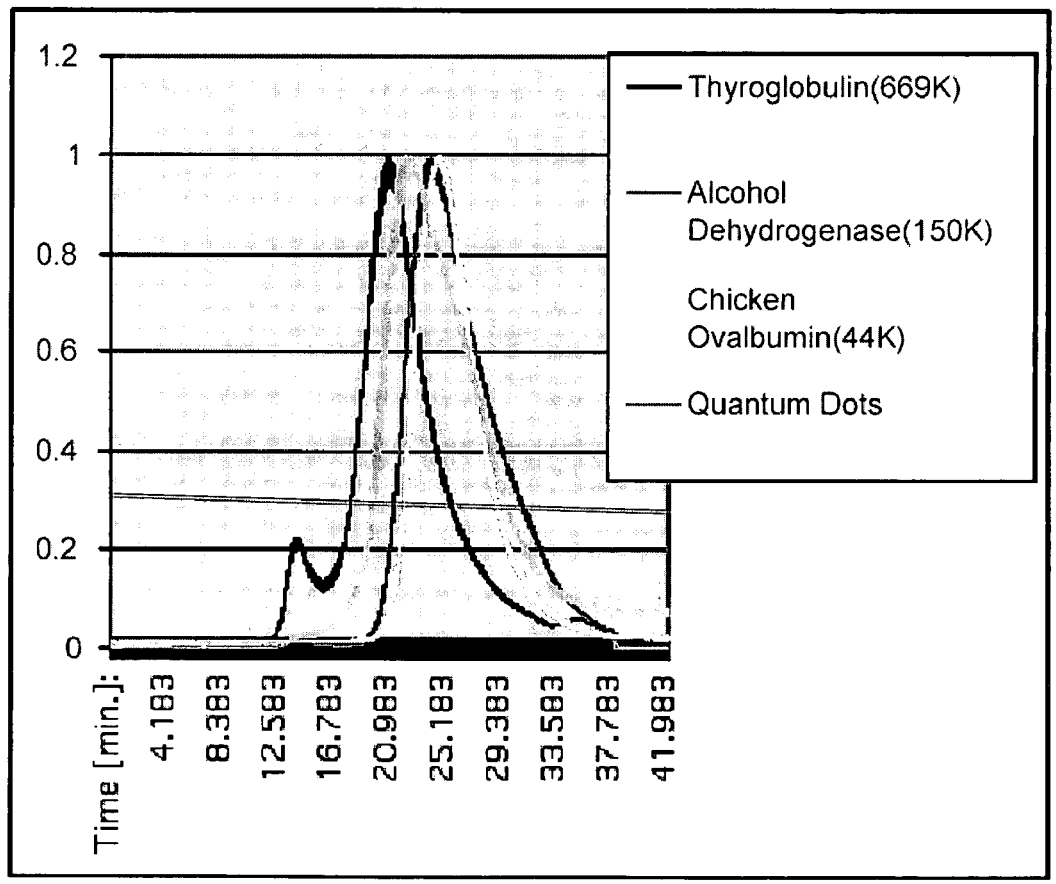
FIG. 1B is a graph depicting photoproperties of the near-infrared nanocrystals.
Figure 6:
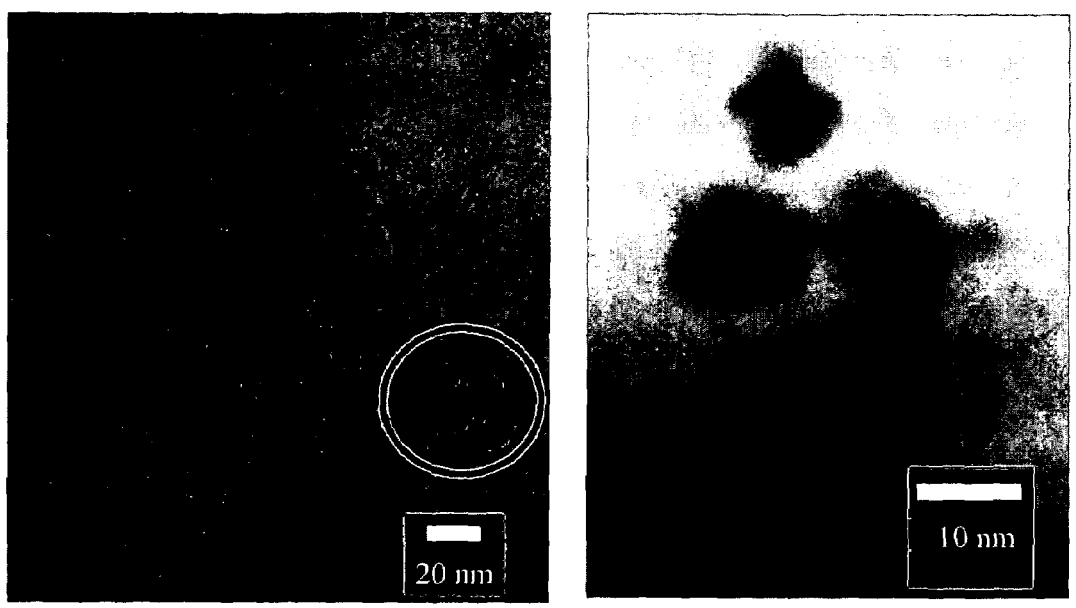
FIG. 6 is a photograph depicting bright field TEM images of CdTe/CdSe(core/shell)nanocrystals.

Preparation of Aqueous Soluble CdTe(CdSe) core(shell) semiconductor nanocrystals. The CdTe(CdSe) composition included a core of cadmium telluride (CdTe) and a thin shell of cadmium selenide (CdSe). Unless otherwise noted, all reactions were carried out in a dry nitrogen atmosphere using a glove box or standard Schlenk techniques. Precipitated CdTe nanocrystals were dispersed in a mixture of trioctylphosphine(TOPO, Alfa, 90%) and trioctylphosohine (TOP, Fluka, 90%), and dried under vacuum at 140° C. Overcoating stock solutions were prepared by combining a 1:1 molar stoichiometry of dimethylcadmium (Strem, 97%) and bis-(trimethylsilyl)selenide in trioctylphosphine (TOP, Fluka, 90%). The CdTe TOPO and TOP mixture was vigorously stirred and heated to 100° C., the prepared overcoating stock solution was then added slowly dropwise. The reaction mixture was stirred for 3 hours at 100° C. The formation of small CdSe nanocrystals (informally called "magic size" nanocrystals, with a peak absorbance at ~410 nm) was monitored by optical spectroscopy. The reaction temperature is raised to 200° C. and kept stirred until the CdSe shell growth is completed. The small "magic size" CdSe nanocrystals fused onto the CdTe nanocrystal core surface, forming a CdSe shell. This process was followed by optical spectroscopy (FIG. 1B), transmission electron microscopy (TEM) (FIG. 6), and photoluminescence life time measurements. The region circled on the left image has been magnified, and shown on the right. TEM instrument JEOL 2000 was operated at 200 kV. The CdSe shell formation step took up to a few days. In FIG. 1B, CdTe(CdSe) core(shell) semiconductor nanocrystals with peak fluorescent emission at 860 nm were prepared and resuspended in PBS at a concentration of 1 μM. Extinction coefficient is shown on the left axis (thick solid line) and photoluminescence (500 nm excitation) is shown on the right axis (dashed line), both as a function of wavelength.

Extensive characterization of such semiconductor nanocrystals using transmission electron microscopy (TEM), x-ray diffraction and fluorescence lifetime measurements show that the structure is consistent with the core consisting of CdTe and a shell of CdSe. See, for example, for example, U.S. Ser. No. 09/732,013, filed Dec. 8, 2000, U.S. Ser. No. 60/402,726, filed Aug. 13, 2002, and U.S. Ser. No. 10/638, 546, filed Aug. 12, 2003, each of which is incorporated by reference in its entirety.

The semiconductor nanocrystals were dispersed in water by exchanging the organic caps with oligomeric phosphines derivatized with carboxylic acid (OPCA) as follows. See, for example, U.S. Ser. No. 60/403,367, filed Aug. 15, 2002, which is incorporated by reference in its entirety. The semiconductor nanocrystal sample was re-dispersed in chloroform. A water solution of OPCA was introduced, forming a bilayer. This mixture was sonicated until all the semiconductor nanocrystals were transferred to the aqueous phase, as determined by the transfer of color from the organic phase to the aqueous phase. Excess OPCA was removed by dialysis. Concentration was determined as described in Leatherdale et al., *J. Phys. Chem. B.* 106:7619–7622 (2002), which is incorporated by reference in its entirety.

Nanocrystals were synthesized in organic solvents and are not usually soluble in aqueous environments. To make soluble, a coating has to be used. The particular coating used in this invention is a polydentate phosphine ligand (OPCA).

Example of a Procedure for Synthesizing OPCA and Ligand Exchange:

Synthesis of the OPCA ligand: 8.00 g Trishydroxypropylphosphine (THPP, Strem, 90%) was dissolved in 20.0 g Dimethylformamide (DMF, Aldrich, 99.8%). 4.54 g Diisocyanatohexane (DIH, Aldrich, 98%) was added dropwise at room temperature, while the solution was vigorously stirred. The solution was stirred for a day after completion of the addition. 19.35 g Ethylisocyanatoacetate (EIA, Aldrich, 95%) was added dropwise at room temperature, and kept stirred for a day. The solvent and excess EIA are removed at 100° C. in vacuo.

Ligand-exchange of CdTe/CdSe(core/shell) QDs with oligomeric phosphine ligands: A CdTe/CdSe(core/shell) nanocrystal powder free of excess TOPO or TOP was obtained by previously described nonsolvent-precipitation methods. Anhydrous methanol was used for the nonsolvent, and the powder is collected after centrifugation. 100 mg CdTe/CdSe(core/shell) nanocrystals, 3.0 g oligomeric phosphine ligands, ~10 mL anhydrous Tetrahydrofuran (THF), and ~2 mL N,N-dimethylformamide(DMF) were rigorously mixed together. The amounts of THF and DMF were chosen so as to make the solution homogeneous. The solution was stirred for an hour. The solvents (THF and DMF) were removed at 100° C. in vacuum. The remaining viscous mixture solution was kept at 120° C. for 3 hours, and cooled to room temperature.

Hydrolysis of the Oligomeric Phosphine Ligand and Purification:

To the sample prepared by above, 50 mL 1.0M sodium hydroxide (NaOH) aqueous solution was added. A stir bar was placed at the interface between the viscous nanocrystal solution and the NaOH solution and stirred vigorously at room temperature. The stirring was continued until the mixture was no longer phase separated and became a slightly turbid dark brown color. The solution was passed through 0.2 μM pore-sized filters and a filtered clear solution was obtained. The solvent was exchanged to a PBS buffer by continuous diafiltration using 50K nominal molecular weight limit membranes.

Tissue Preparation. Human whole blood was collected directly into a purple top (EDTA) clinical specimen tube and stored at 4° C. Where indicated, it was diluted in phosphate-buffered saline, pH 7.4 (PBS) supplemented with 5 mM EDTA (to prevent clotting). Skin was prepared by surgical excision and bathed in ice cold PBS. Specimens were used within 3 hours of collection.

Absorbance Measurements. Pairs of optically matched 1.0 cm or 0.05 cm cuvettes (Spectrocell, Oreland, Pa.) were used on a Model 5 (Varian-Cary, Palo Alto, Calif.) scanning spectrophotometer equipped with deuterium and tungsten lamps. Absorbance wavelength scans from 400 nm to 2000 nm, at a resolution of 1 nm, were performed on water (air blank), lipid (olive oil; air blank), OxyHb in PBS, DeoxyHb in PBS, and protein (albumin) in PBS (PBS blank). Five individual scans were averaged prior to calculation of the extinction coefficient at each wavelength. Measured values matched closely those described in Conway et al., *Am. J. Clin. Nutr.* 40:1123–1130 (1984); and Kuenstner et al., *Biospectroscopy* 3:225–232 (1997), which is incorporated by reference in its entirety.

Figure 2:
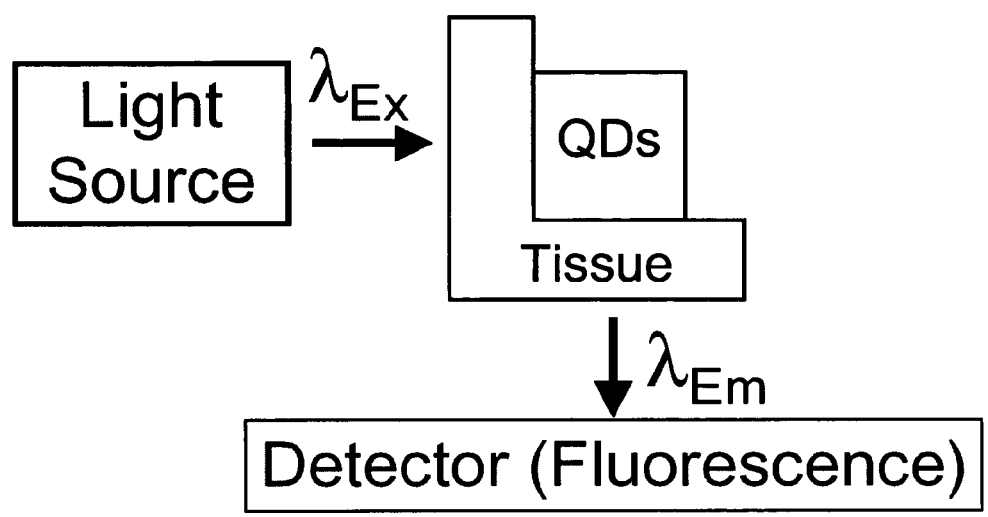
FIGS. 2A–D are drawings depicting an experimental geometry and nanocrystal performance in scattering and/or absorbing media and tissue.
Figure 2:
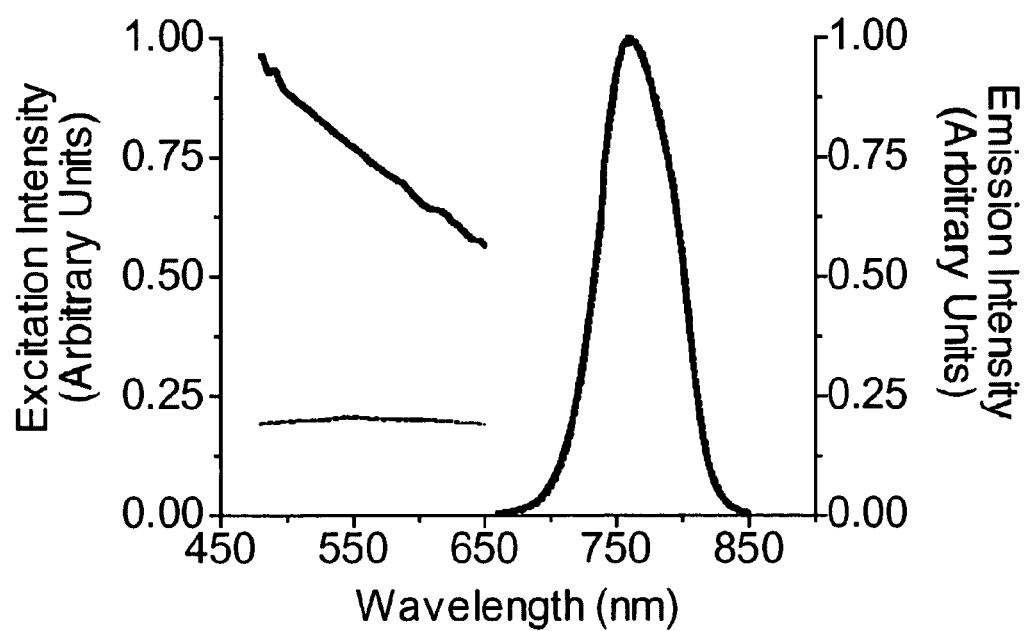
Figure 2:
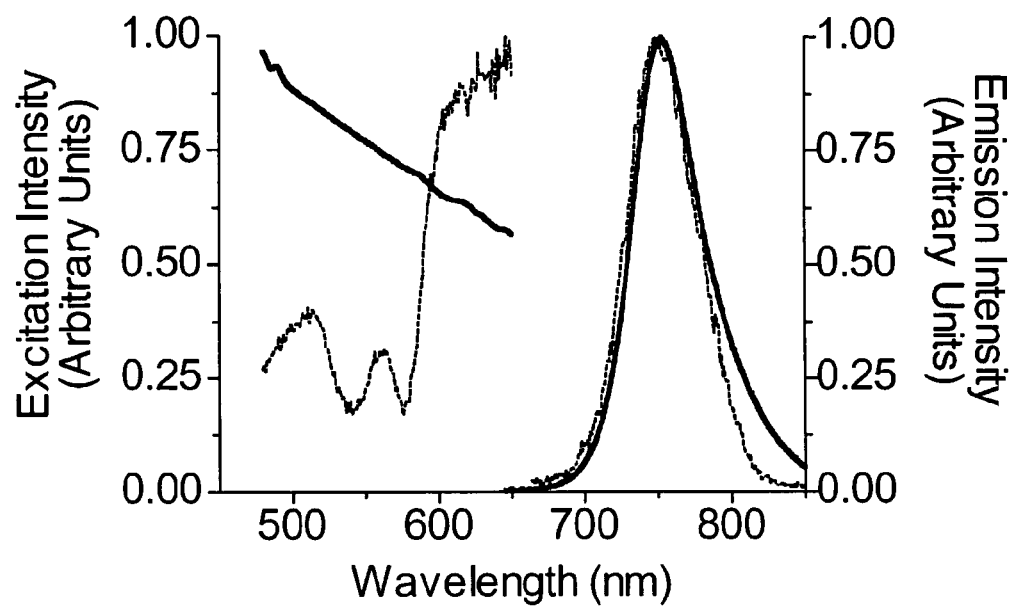
Figure 2:
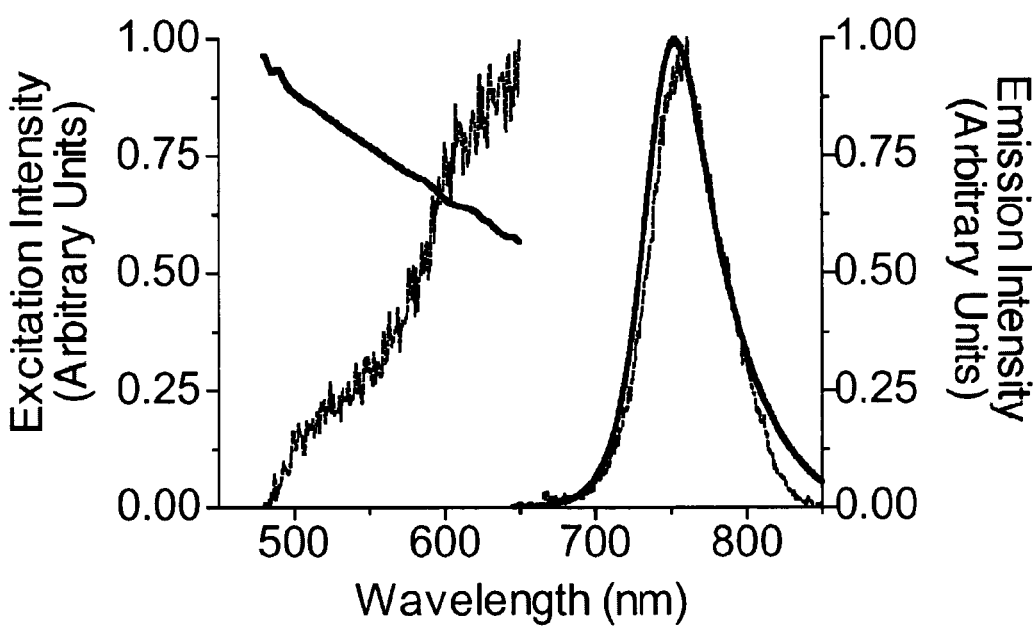

Scanning Spectrofluorometry. Fluorescence excitation and emission scans were performed on a SPEX Fluorolog-2 spectrofluorometer (Jobin Yvon Horiba, Edison, N.J.) equipped with a R928 photomultiplier tube. To preserve high quantum yield (QY), non-OPCA treated semiconductor nanocrystals were diluted to 1 μM in hexane and placed in a 1 cm path length cuvette sandwiched by different in vivo simulating media, or tissue, as shown in FIG. 2A, in which the illumination/detection geometry of spectrophotometer experiments is shown. Excitation light ($\lambda_{Ex}$) was a single, thin collimated beam propagating through optically thin tissue. Semiconductor nanocrystals at the given concentration were below the tissue and absorb the net excitation photons. Depending on the quantum yield of the semiconductor nanocrystals, fluorescent light ($\lambda_{Em}$) was emitted and propagated out through the same thickness of tissue. The detector was placed at 90° relative to the excitation light beam.

Modeling semiconductor nanocrystal Performance during In Vivo Imaging. To describe light propagation through tissue, the geometry shown in FIG. 3A was assumed and adapted a previously described analytical solution to the diffusion equation. See, for example, Gardner et al., *Lasers Surg. Med.* 18:129–38 (1996), which is incorporated by reference in its entirety. Briefly, for a given fluence rate, the local rate of energy absorption by semiconductor nanocrystals ($R_A$ in mW/cm³) can be expressed by the extinction (or absorption) coefficient of semiconductor nanocrystals at the excitation wavelength ($\lambda_{Ex}$) as ($\mu_{QDs}(\lambda_{Ex})(cm^{-1})$) and the spatial distribution of the light energy fluence rate $\phi(z, \lambda_{Ex})$ in mW/cm², where z represents depth in the tissue:

$$R_A(z, \lambda_{Ex}) = \mu_{QDs}(\lambda_{Ex}) \cdot \phi(z, \lambda_{Ex})$$

where $\mu_{QDs}(\lambda_{Ex}) = \epsilon_{QDs}(\lambda_{Ex}) \cdot c_{semiconductor\ nanocrystals}$, $\epsilon_{QDs}(\lambda_{Ex})$ is the extinction coefficient per mole of semiconductor nanocrystals and $c_{semiconductor\ nanocrystals}$ is the molar concentration of semiconductor nanocrystals. Since $c_{semiconductor\ nanocrystals}$ did not affect any of the results discussed below, it was held constant in all simulations. The fluence rate $\phi(z, \lambda_{Ex})$ is given by:

$$\phi(z, \lambda_{Ex}) = E_O[D_1 \exp(-k_1 z/\delta) - D_2 \exp(-k_2 z/\delta)]$$

where $E_o$(mW/cm²) is the incident fluence rate (for all simulations, $E_0$ was held constant at 50 mW/cm² at each wavelength), and $\delta$ is the effective penetration depth, defined from diffusion theory as:

$$\delta = \frac{1}{\sqrt{3\mu_a(\mu_a + \mu'_s)}}$$

where $$\mu_a = \sum_{i=1} \mu(\lambda)_{a,i} c_i \text{ and } \mu'_s = \sum_{i=1} \mu'(\lambda)_{s,i} c_i$$

Here, $\mu_a(\lambda)(cm^{-1})$ and $\mu'_s(\lambda)(cm^{-1})$ represent the total tissue absorption and reduced scattering coefficients, respectively, and $\mu_{a,i}(\lambda)(M^{-1}cm^{-1})$ and $\mu'_{s,i}(\lambda)(M^{-1}cm^{-1})$ represent the absorption and scatter coefficients, respectively, of individual biomolecules at the particular excitation or emission wavelength, and at a concentration $c_i$(M), which comprise the tissue. Values for $\mu_a$ of water, lipid, DeoxyHb, OxyHb, and protein were measured as described above. The relationship between scattering coefficient and wavelength ($\lambda$) can be empirically described as follows: $\mu'_s(\lambda) = J\lambda^{-P}$, where J is related to the scattering density and P is the scatter power coefficient. See, for example, Mourant et al., *Appl. Opt.* 36:949–957 (1997), which is incorporated by reference in its entirety. The parameters $D_1$, $k_1$, $D_2$, $k_2$ (and $D_3$, $k_3$, see below) depend solely upon diffuse reflectance, $R_d$, aspects of which have been previously investigated through Monte Carlo simulations (see, Gardner et al., *Lasers Surg. Med.* 18:129–138 (1996)):

$$D_1 = 3.04 + 4.90 R_d - 2.06 \exp(-21.1 R_d)$$

$$k_1 = 1 - (1 - 1/\sqrt{3}) \exp(-18.9 R_d)$$

$D_2=2.04-1.33R_d-2.04\exp(-21.1R_d)$ $k_2=1.59\exp(3.36R_d)$

For simplicity, the refractive index of tissue was assumed to be 1.33 as for all simulations. The value of $R_d$ depends on the absorption coefficient of the tissue and the effective path length that photons travel in the tissue, and can be approximated as a function of N', defined as the ratio of reduced scattering coefficient to absorption ($\mu'_s/\mu_a$). The diffuse reflectance, $R_d$, from the surface of a semi-infinite medium is approximated by the expression (see, Jacques, Vol. 1999, Oregon Medical Laser Center News (1999), which is incorporated by reference in its entirety):

$$R_d \approx \exp(-A\delta\mu_a) = \exp\left(-\frac{A}{\sqrt{3(1+N')}}\right)$$

where $$A = 6.3744 + 0.35688 \exp(\ln(N')/3.4739)$$

The factor A δ equals the apparent path length L for photon attenuation due to the absorption coefficient. A is approximately 7–8 for most soft tissues. See, Jacques, Vol. 1999, Oregon Medical Laser Center News (1999). These analytical expressions have accuracy comparable to Monte Carlo simulations over an essentially unrestricted range of diffuse reflectance values. See Gardner et al., *Lasers Surg. Med.* 18:129–38 (1996). The rate of semiconductor nanocrystal emission ($R_E$ in mW/cm$^3$) is given by:

$R_E(z, \lambda_{Ex}, \lambda_{Em})=R_A(z, \lambda_{Ex})\cdot QY(\lambda_{Em})\cdot G(z, \lambda_{Em})$ Where $QY(\lambda_{Em})$ represents the QY of semiconductor nanocrystals at the emission wavelength ($\lambda_{Em}$). $G(z, \lambda_{Em})$ or the escape function, which describes the exponential decay of emitted light from an isotropic point source at depth z (see, Gardner et al., *Lasers Surg. Med.* 18:129–38 (1996)), is given by:

$G(z, \lambda_{Em})=D_3\exp(-k_3 z/\delta)$ where:

$D_3=0.32+0.72R_d-0.16\exp(-9.11R_d)$ $k_3=1-0.30\exp(-6.12R_d)$

In the case of broadband excitation light, the source and excitation spectrum must be integrated over all incident wavelengths. Thus, the above equation can be re-written as follows:

$R_E(z, \lambda_{Ex}, \lambda_{Em})=\Sigma_i[R_A(z, \lambda_{Ex,i})\cdot QY(\lambda_{Em})\cdot G(z, \lambda_{Em})]$ The light intensity of $R_A$ or $R_E$ at any one wavelength can be converted to number of photons per cm$^3$ ($N_{A,E}$) by the following formula:

$$N_{A,E} = \frac{R_{A,E}}{1.99 \times 10^{-16}/\lambda(\text{nm})}$$

If desired, the geometry of the semiconductor nanocrystal source can be used to convert $N_{A,E}$ into units of mW/cm$^2$. These equations, along with the attenuation curves for water, lipid, OxyHb, DeoxyHb, and protein were incorporated into an Excel 98 spreadsheet (Microsoft, Redmond, Wash.) for rapid analysis of model variables. The model is available from the authors as an Excel spreadsheet.

In Vivo NIR Fluorescence Imaging. Imaging was performed as described in Nakayama et al., "Functional near-infrared fluorescence imaging for cardiac surgery and targeted gene therapy," *Molecular Imaging* (2002), except no laser was used, and only a single 150 W halogen light source illuminated the surgical field. A combination of hot mirrors and band pass filters (Chroma, Brattleboro, Vt.) produced broadband excitation light of 400 nm to 700 nm at a total fluence rate of 2.0 mW/cm$^2$. A 740 dcxr dichroic mirror (740 nm center point) and model D770/50 emission filter (745 nm to 795 nm) were also purchased from Chroma. The Orca-ER (Hamamatsu, Bridgewater, N.J.) NIR camera settings included gain 7 (out of 9), 2×2 binning, 640×480 pixel field of view, and exposure time of 25 msec. Color video camera (HV-D27, Hitachi, Tarrytown, N.Y.) images were acquired at 30 frames per second at a resolution of 640×480 pixels. Data was acquired and quantitated on a Macintosh computer equipped with a Digi-16 Snapper (DataCell, North Billerica, Mass.) frame grabber (for Orca-ER), CG-7 (Scion, Frederick, Md.) frame grabber (for HV-D27) and IPLab software (Scanalytics, Fairfax, Va.). Aqueous soluble semiconductor nanocrystals were resuspended in PBS. The suspension was injected and imaged as described in the text and in Nakayama et al., "Functional near-infrared fluorescence imaging for cardiac surgery and targeted gene therapy," *Molecular Imaging* (2002).

Synthesis of Aqueous Soluble NIR Emitting Semiconductor Nanocrystals

Based on an analysis of transmission bands in biological tissue having different properties (discussed in detail below), NIR semiconductor nanocrystals with a peak emission wavelength at 860 nm were synthesized. Extensive characterization using transmission electron microscopy, x-ray diffraction and fluorescence lifetime measurements show that the structure is consistent with a core consisting of CdTe and a shell of CdSe (data not shown), and a mean diameter of approximately 15–20 nm. Semiconductor nanocrystals were made soluble in aqueous media by treatment with oligomeric phosphines. The extinction coefficient of these NIR semiconductor nanocrystals feature the characteristic increase to the blue, with a shoulder at approximately 730 nm. Scanning spectrofluorometry showed a peak emission at 860 nm (FIG. 1B).

Semiconductor Nanocrystal Performance with Scattering Medium

The influence and attenuation properties of surrounding tissue on absorbance and emission properties of 752 nm emissive semiconductor nanocrystals was determined. The experimental geometry is shown in FIG. 2A. The first medium chosen was simply a non-absorbing buffer (PBS) into which was added increasing concentrations of Intralipid. Intralipid is a suspension of various lipids in water that is often used to simulate tissue scatter, and exhibits scatter that is strongly-dependent on wavelength (proportional to $\approx\lambda^{-2.4}$, see, for example, van Staveren et al., *Applied Optics* 30:4507–4514 (1991), which is incorporated by reference in its entirety). Shown in FIG. 2B is the effect of increasing scatter on NIR semiconductor nanocrystal excitation. In the absence of scatter (thick solid line), scanning spectrofluorometry confirmed that fluorescence excitation matches the pattern of absorbance shown in FIG. 1. However, with as little as 0.02% Intralipid ($\mu_s'\approx 0.3$ cm$^{-1}$ at 630 nm), increased semiconductor nanocrystal absorbance at bluer wavelengths was lost. The effect of 0.02% Intralipid on semiconductor nanocrystal emission was insignificant (FIG. 2B, semiconductor nanocrystal fluorescence excitation (left) and emission (right) in 0.02% Intralipid (dashed line)). The semiconductor nanocrystals shown in FIG. 1 were subjected to excitation and emission spectrofluorometry, as described in Materials and Methods, using the geometry shown in FIG. 2A. For excitation scans (left curves), the emission wavelength was fixed at 752 nm. For emission scans (right curves), the excitation wavelength was fixed at 550 nm (Intralipid) or 650 nm (blood, skin). For comparison, semiconductor nanocrystal performance in PBS is shown on each graph (thick solid line). Data were normalized for display on a single ordinate.

Semiconductor Nanocrystal Performance with Tissues Having Absorbance and Either Wavelength-Independent or Wavelength-Dependent Scatter The effect of surrounding biological tissue on performance of semiconductor nanocrystals was studied. For these experiments, human whole blood was chosen as an absorbing tissue whose scatter was independent of wavelength, and non-pigmented hairless mouse skin as a tissue whose scatter was dependent on wavelength. See, for example, Cheong et al., *IEEE J. Quantum Electronics* 26, 2166–2195 (1990). As shown in FIG. 2C (left curves), semiconductor nanocrystals surrounded by even dilute human blood had a complex wavelength-dependent excitation spectrum, which differed markedly from the predicted semiconductor nanocrystal absorbance in non-absorbing and non-scattering medium. Most importantly, increasing absorption at bluer wavelengths was absent. The wavelength dependence of emission was fairly symmetrical about the predicted peak emission of 752 nm (FIG. 2C, right curves) (semiconductor nanocrystal fluorescence excitation (left) and emission (right) in human whole blood (i.e., a tissue exhibiting wavelength-independent scatter) diluted 50-fold (dashed line)). The loss of bluer wavelength in the semiconductor nanocrystal excitation spectrum was even more pronounced at higher blood concentrations (data not shown). As shown in FIG. 2D (left curves) (semiconductor nanocrystal fluorescence excitation (left) and emission (right) in 0.99 mm thick non-pigmented hairless mouse skin (i.e., a tissue exhibiting wavelength-dependent scatter)), the excitation spectrum of semiconductor nanocrystals surrounded by hairless mouse skin exhibited essentially a compete loss of bluer wavelengths, and semiconductor nanocrystal emission was slightly red-shifted.

These data and additional simulations (not shown) indicate that biological tissue exhibits a "filter" effect that can counteract the advantageous increase in semiconductor nanocrystal absorbance at bluer wavelengths. This effect was highly dependent on the shape of the semiconductor nanocrystal absorbance curve and the shapes and strengths of the tissue absorbance and scatter attenuation curves. Furthermore, when the tissue scatter power coefficient is high, there can be a red-shift of peak semiconductor nanocrystal emission.

Selection of Semiconductor Nanocrystal Peak Emission wavelengths Based on Tissue Transmission Bands For reflectance fluorescence imaging, the light source is typically uniform and diffuse, and perpendicular to the air/tissue interface. Since semiconductor nanocrystals will likely be used in the future for tumor targeting, and specifically for the detection of small collections of malignant cells, in the analysis they are assumed to be concentrated at a point, at a depth z below the air/tissue interface (FIG. 3A). The illumination/detection geometry used for predicting the performance of semiconductor nanocrystals for reflectance fluorescence imaging assumes continuous wave, uniform irradiance normal to the air/tissue interface, a semi-infinite thick tissue, and a point of semiconductor nanocrystals embedded in the tissue at a given depth. Fluorescent light emitted by the semiconductor nanocrystals propagates back through the tissue and is detected at 0° relative to excitation light. Adapted from Gardner et al., *Lasers Surg. Med.* 18:129–138 (1996). An analytical solution to the diffusion equation that matches this imaging geometry, and have validated its accuracy against Monte Carlo simulations is described in, for example, Gardner et al., *Lasers Surg. Med.* 18:129–38 (1996).

Using this model in spreadsheet format (see Materials and Methods), semiconductor nanocrystal performance can be simulated under conditions of varying absorbance, scatter, tissue thickness, and semiconductor nanocrystal optical properties. In most tissues, absorbance is dominated by $H_2O$ and hemoglobin (Hb), each of which has local minima and maxima of transmission. Although total photon transmission is a continuum, to simplify the analysis, four transmission "bands" shown in FIG. 3B were studied: 690 nm to 915 nm (Band 1), 1025 to 1150 (Band 2), 1225 nm to 1370 nm (Band 3), and 1610 nm to 1710 nm (Band 4). The lower limit of Band 1 is bounded by Hb absorbance, whereas its upper limit is bounded by lipid and $H_2O$ absorbance. All other transmission bands represent local minima in the $H_2O$ absorption curve. Band 4 ends at 1710 in this analysis to avoid a sharp lipid absorbance peak at 1735 nm (data not shown). See, for example, Kou, L. et al., *Appl. Opt.* 32:3531–3540 (1993), which is incorporated by reference in its entirety.

Shown simulated in FIG. 3B are the number of photons transmitted through tissues of varying $H_2O$ to Hb ratio, scatter power coefficient, and thickness, as a function of wavelength. Using the model geometry shown in FIG. 3A, the number of transmitted photons as a function of wavelength was simulated on tissues of high $H_2O$ to Hb ratio (left panels) or high Hb to $H_2O$ ratio (right panels), at tissue thicknesses of 0.25 cm (thick solid line) or 1 cm (dashed line). Simulated tissues exhibited either wavelength-independent scatter (upper panels) or wavelength-dependent scatter (lower panels). The analysis identified four possible transmission bands (black bars below ordinate) as described in the text. The arrow above each transmission band identifies the peak semiconductor nanocrystal emission wavelength used for subsequent analysis. For simplicity, the OxyHb to DeoxyHb ratio was fixed at one to one, and lipid content was fixed at 15% by weight (i.e., 0.25 M assuming an average lipid molecular weight of 600 Da and an equal ratio of cholesterol and phosphatidylcholine). Model parameters used for the simulation included: thickness as shown, water content=75%, lipid content=0.25 M, OxyHb concentration=1.25 or 0.02 mM, DeoxyHb concentration=1.25 or 0.02 mM, protein concentration=2.5 mM, absolute scatter at 630 nm=8.9 $cm^{-1}$ (wavelength-independent scatter) or 23 $cm^{-1}$ (wavelength-dependent scatter), and scatter power coefficient=0 (wavelength-independent scatter) or 2.81 (wavelength-dependent scatter). These model parameters were chosen to match previously described parameters (see, Cheong et al., *IEEE J. Quantum Electronics* 26:2166–2195 (1990)) for blood (wavelength-independent scatter) and skin (wavelength-dependent scatter). 400 nm was chosen as a lower limit for the simulation since ultraviolet light penetrates poorly into tissue, and 2000 nm was chosen as the upper limit due to water's extreme absorption above this wavelength.

For a scatter power coefficient of zero (i.e., wavelength-independent scatter; FIG. 3B, upper), relative transmission was highly influenced by both the $H_2O$ to Hb ratio and tissue thickness. In particular, at a high Hb to $H_2O$ ratio, transmission through Bands 1, 2 and 4 decreased more rapidly than through Band 3 with increasing thickness, and at all $H_2O$ to Hb ratios, transmission through Band 4 had the most rapid decrease with increasing thickness. Relative transmission through Bands 1 and 2 were affected similarly by tissue thickness (significantly less than through Bands 3 and 4) in the presence of a high $H_2O$ to Hb ratio, and transmission through Band 3 was the least affected by tissue thickness in the presence of a high Hb to $H_2O$ ratio.

For a high scatter power coefficient (i.e., wavelength-dependent scatter; FIG. 3B, lower) the patterns of transmission were similar to those found for wavelength-independent scatter, but overall, relative transmission favored longer wavelengths. These transmission results were consistent with previous empirical measurements and serve to guide the choice of optimal semiconductor nanocrystal emission wavelengths. See, for example, Wan et al., *Photochem. Photobiol.* 34:679–681 (1981); Anderson and Parrish, *J. Invest. Dermatol.* 77:13–19 (1981); and Du et al., *Phys. Med. Biol.* 46:167–81 (2001), each of which is incorporated by reference in its entirety.

Simulated Performance of Various NIR and IR Semiconductor Nanocrystal Contrast Agents The performance of semiconductor nanocrystals with peak emission in Bands 1 through 4 after embedding in tissues with varying $H_2O$ to Hb ratios and scatter power coefficients was simulated. For simplicity, tissue thickness was fixed at 0.5 cm. Semiconductor nanocrystal peak emission was chosen at two thirds the width of the transmission band to provide enough bandwidth to accommodate excitation close to the emission wavelength (if needed) and the broader emission curves associated with longer wavelength semiconductor nanocrystals. To eliminate variability due to the shape of the semiconductor nanocrystal absorption curve (itself a function of the semiconductor materials used and particular preparation; see Discussion) and aqueous QY (a function of the semiconductor materials and surface coating), these parameters were fixed. In particular, the shape of the semiconductor nanocrystal absorption curve used in the simulation is common to many different types of semiconductor nanocrystal materials. See, for example, Leatherdale et al., *J. Phys. Chem. B.* 106:7619–7622 (2002); Guzelian et al., *Applied Physics Letters* 69, 1432–1434 (1996); Cao and Banin, *J. Am. Chem. Soc.* 122:9692–9702 (2000); and Murray et al., *IBM Journal of research and Development* 45:47–56 (2001), each of which is incorporated by reference in its entirety. The emission curve was simulated with a Gaussian distribution. FWHMs for 840 nm, 1110 nm, 1320 nm, and 1680 nm semiconductor nanocrystals were chosen based on literature and empirical data, and were 76 nm, 104 nm, 145 nm, and 235 nm, respectively. QY was fixed at 50%, and the extinction coefficient at the first absorption peak was fixed at $1\times10^6$ $M^{-1}cm^{-1}$. Other model parameters used for this simulation included: broadband excitation from 400 nm to the peak emission wavelength using a constant fluence rate at each wavelength, thickness 0.5 cm, water content=75%, lipid content=0.25 M, OxyHb concentration=1.25 or 0.02 mM (1 to 1 ratio with DeoxyHb), DeoxyHb concentration=1.25 or 0.02 mM, protein concentration=2.5 mM, absolute scatter at 630 nm=8.9 $cm^{-1}$ (wavelength-independent scatter) or 23 $cm^{-1}$ (wavelength-dependent scatter), and scatter power coefficient=0 (wavelength-independent scatter) or 2.81 (wavelength-dependent scatter).

Figure 4:
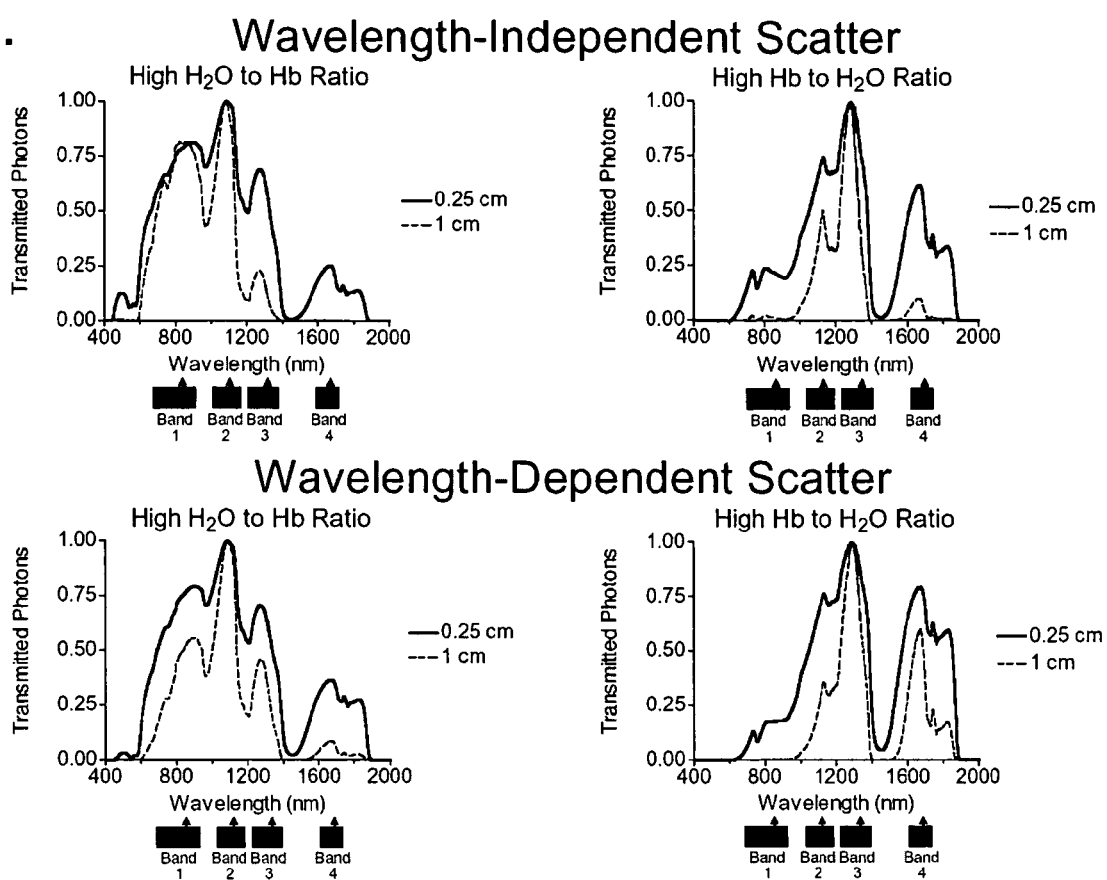
FIG. 4 is a graph depicting predicted absorbance of NIR and IR semiconductor nanocrystals as a function of tissue scatter, $H_2O$ to Hb ratio, and thickness.

As shown in FIG. 4, semiconductor nanocrystal performance was predicted to be affected significantly by tissue optical properties. Absorbance scans for various semiconductor nanocrystals embedded in tissue with either wavelength-independent scatter (left panels) or wavelength-dependent scatter (right panels) were simulated as described in the text. Simulations were run in the presence of PBS only (thick solid line) or the presence of 0.5 cm of tissue with a high $H_2O$ to Hb ratio (thin solid line) or high Hb to $H_2O$ ratio (dashed line) as described in the text. Semiconductor nanocrystal peak emission is shown along the left edge of the page. Data are normalized for display on a single ordinate. Specifically, for tissues with a high $H_2O$ to Hb ratio (thin solid curves), the key feature of semiconductor nanocrystal excitation at bluer wavelengths was often preserved, suggesting that broadband excitation light can be used. However, at a high Hb to $H_2O$ ratio (dashed curves), semiconductor nanocrystal excitation fell rapidly below 700 nm. When wavelength-dependent scatter was also present, excitation was further confined to a narrow band close to semiconductor nanocrystal peak emission, with high similarity to the pattern of excitation typically seen using conventional fluorophores. Semiconductor nanocrystal emission (data not shown) was also affected significantly by tissue absorbance and scatter. Specifically, a red shift in peak emission wavelength was often seen in the presence of wavelength-dependent scatter (see also FIG. 2D), and the emission of 1680 nm semiconductor nanocrystals was additionally affected by lipid absorption (not shown).

Figure 5:
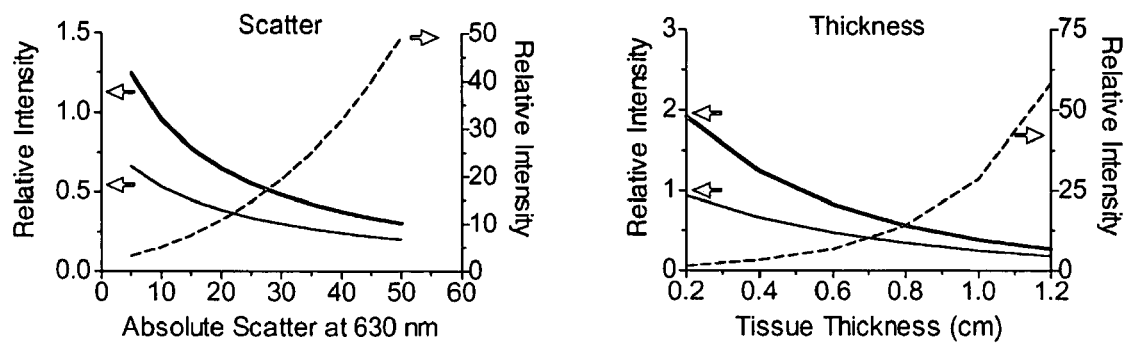
FIGS. 5A–B are graphs depicting comparison of NIR and IR semiconductor nanocrystal performance as a function of tissue scatter, $H_2O$ to Hb ratio, and thickness.
Figure 5:
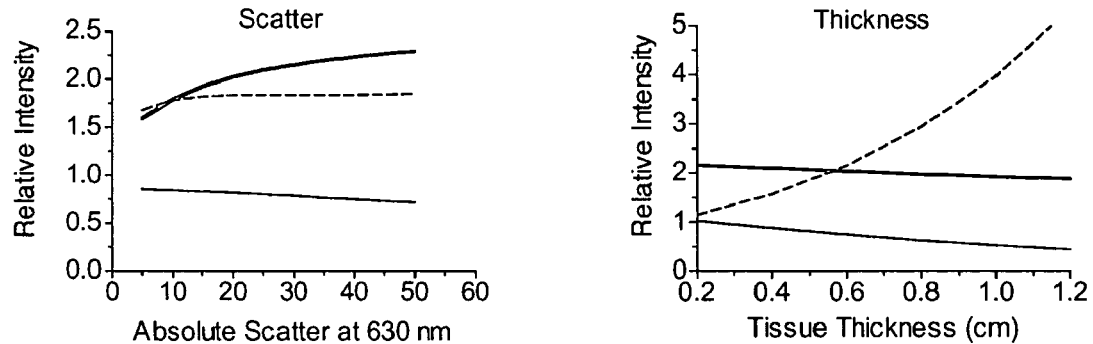

Selection of Semiconductor Nanocrystal Excitation and Emission Wavelengths Based on Photon Yield A direct comparison of semiconductor nanocrystals with emission centered at 840 nm, 1110 nm, 1320 nm, and 1680 nm, as a function of absolute scatter and tissue thickness, is presented in FIG. 5A for a high $H_2O$ to Hb ratio, and FIG. 5B for a high Hb to $H_2O$ ratio. Model parameters were otherwise as described for FIG. 4. Comparison of final photon yield of 840 nm, 1110 nm, 1320 nm, and 1680 nm emitting semiconductor nanocrystals, as a function of tissue scatter and thickness, in tissue with a high $H_2O$ to Hb ratio. Simulated tissues exhibited either wavelength-independent scatter (upper panels) or wavelength-dependent scatter (lower panels). To determine the effect of scatter (left panels), tissue thickness was fixed at 0.5 cm. To determine the effect of tissue thickness, absolute scatter at 630 nm was fixed at 8.9 $cm^{-1}$ (wavelength-independent scatter) or 23 $cm^{-1}$ (wavelength-dependent scatter), and the scatter power coefficient fixed at either 0 (wavelength-independent scatter) or 2.81 (wavelength-dependent scatter). In FIG. 5A, on the ordinate is shown the photon yield as a ratio of 1320 nm semiconductor nanocrystals to either 840 nm semiconductor nanocrystals (thick solid line), 1110 nm semiconductor nanocrystals (thin solid line), or 1680 nm semiconductor nanocrystals (dashed line). Note is again made that excitation was broadband, from 400 nm to the peak emission wavelength, using a constant fluence rate at each wavelength. For simplicity, results are displayed as the ratio of the total photon yield of 1320 nm semiconductor nanocrystals relative to the others.

Over the full range of tissue $H_2O$ to Hb ratio, absolute scatter, scatter power coefficient, and thickness tested, 1680 nm semiconductor nanocrystals performed poorly relative to the others, mainly due to the effect of $H_2O$ absorption. In tissues with a high $H_2O$ to Hb ratio (FIG. 5A), regardless of scatter power coefficient, 1110 nm semiconductor nanocrystals outperformed 840 nm and 1320 nm semiconductor nanocrystals by up to five-fold. In the presence of wavelength-dependent scatter, 1320 nm semiconductor nanocrystals outperformed 840 nm semiconductor nanocrystals, but only up to two-fold.

The simulation described in FIG. 5B was repeated in tissue with a high Hb to H2O ratio. In contrast, in the presence of a high Hb to $H_2O$ ratio (FIG. 5B), 1320 nm semiconductor nanocrystals outperform 840 nm semiconductor nanocrystals by 32-fold to $5 \times 10^3$ fold, and 13-fold to $1 \times 10^6$ fold, over the tested range of scatter and thickness, respectively, with the highest performance in tissues with wavelength-dependent scatter. 1320 nm semiconductor nanocrystals also outperform 1110 nm and 1680 nm semiconductor nanocrystals, but by a less significant magnitude. The significance of these results for imaging applications is discussed below.

NIR Fluorescence Imaging with Semiconductor Nanocrystals using Broadband White Light Excitation An intraoperative NIR fluorescence imaging system that can be used with conventional fluorophores such as indocyanine green and IRDye78 for real-time assessment of coronary vasculature in beating hearts can be used here. See, for example, Nakayama et al., "Functional near-infrared fluorescence imaging for cardiac surgery and targeted gene therapy," *Molecular Imaging* (2002). Conventional fluorophores, however, absorb in a relatively narrow wavelength band, and typically require a separate NIR (770 nm) laser light source for excitation. Advantageously, NIR semiconductor nanocrystals can be used in place of conventional fluorophores for vascular imaging, and a single white light source can replace laser excitation, and can be used for both standard illumination and semiconductor nanocrystal fluorescence excitation.

Figure 3:
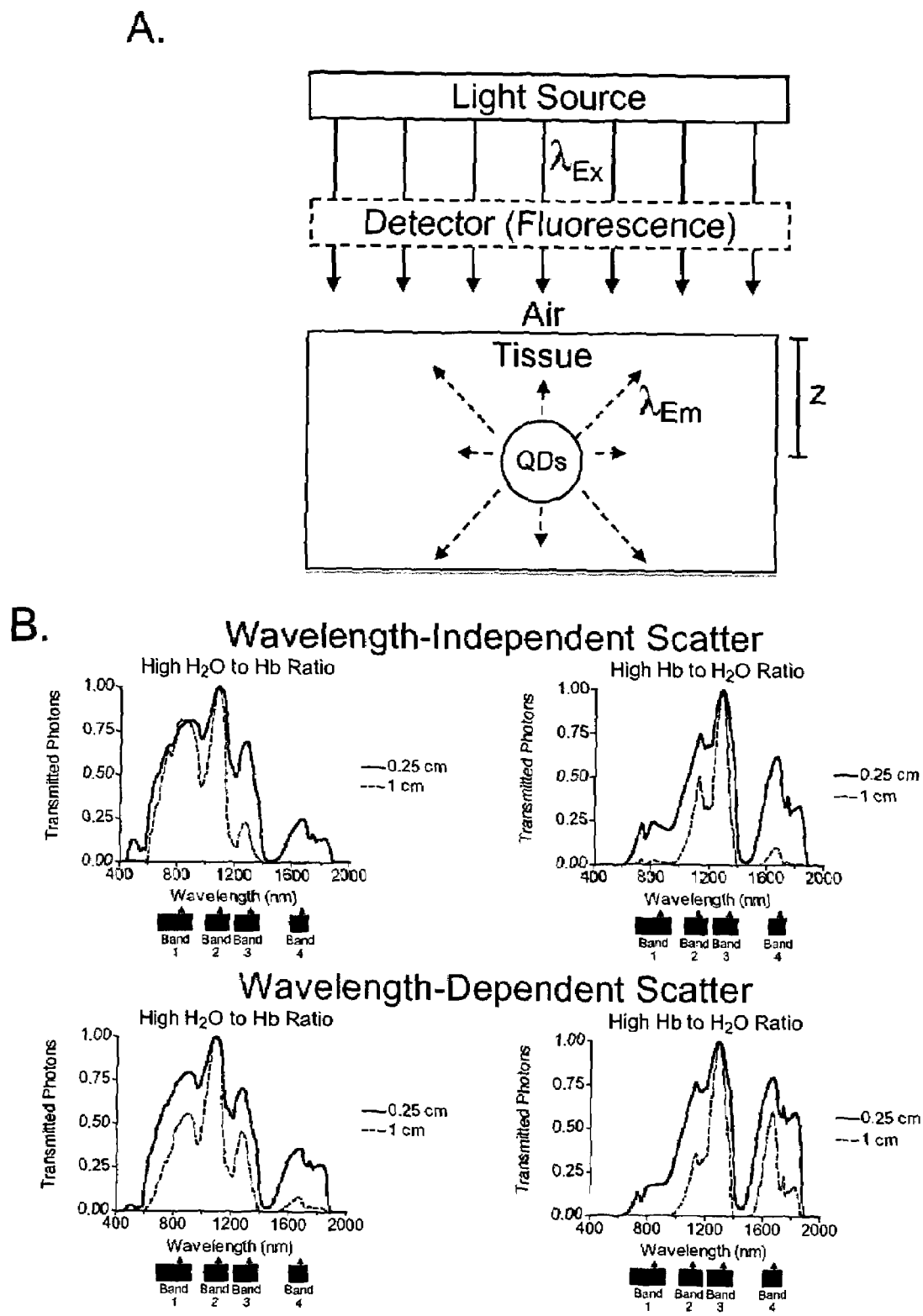
FIGS. 3A–B are graphs depicting predicted photon transmission properties of biological tissue as a function of scatter, $H_2O$ to Hb ratio, and thickness.

FIGS. 2C, 3, and 4 suggest that for tissues with wavelength-independent scatter and a high Hb to $H_2O$ ratio, such as blood, semiconductor nanocrystals with a peak emission within transmission Band 1 might perform well, provided that tissue thickness is minimal. To choose a semiconductor nanocrystal emission wavelength optimal for the silicon-based CCD camera, the model in spreadsheet format was used to compare semiconductor nanocrystals spanning Band 1. It was determined (data not shown) that semiconductor nanocrystals having peak emission at 752 nm would maximize the number of photons collected by the camera, and these particular NIR semiconductor nanocrystals were synthesized as described above.

The goal of this study was to better understand how tissue absorbance, scatter, and thickness might affect the performance of semiconductor nanocrystals when embedded in biological tissue and used as contrast agents for biomedical assays and imaging. This is based on the assumption that the excitation fluence at the semiconductor nanocrystals is within their linear response regime, and well below their saturation limit. The saturation limit of 840 nm semiconductor nanocrystals is estimated to be on the order of $\sim 1$ $kW/cm^2$, and from Fermi's golden rule, $\sim 0.25$ $kW/cm^2$ for 1320 nm semiconductor nanocrystals. Indeed, the vascular imaging data was obtained with an external excitation fluence rate of only 2.0 $mW/cm^2$.

Biological tissue can have a dramatic filtering effect on semiconductor nanocrystal absorbance (FIGS. 2B–D). Using a previously validated mathematical model that fits well the geometry of reflectance fluorescence imaging, testable hypotheses were formulated regarding the selection of semiconductor nanocrystal wavelengths for biomedical applications. The data suggest that the magnitude of tissue scatter, the scatter power coefficient, tissue thickness, and the ratios of absorbing components can have profound effects on semiconductor nanocrystal excitation and emission wavelength choice. Despite the complexity of a model with many independent variables, several generalizations can be inferred from the data.

In tissues with a high $H_2O$ to Hb ratio and either wavelength-independent scatter (e.g., post-menopausal breast) or wavelength-dependent scatter (e.g., skin), the unique and desired property of semiconductor nanocrystals, namely increasing excitation at bluer wavelengths, is largely preserved (FIG. 4, solid line), and semiconductor nanocrystals emitting in Bands 1, 2, or 3 (FIG. 5A) should perform well, with a slight overall advantage for Band 2.

In tissues with a high Hb to $H_2O$ ratio (e.g., blood), regardless of scatter type, 1320 nm semiconductor nanocrystals outperform 840 nm semiconductor nanocrystals by up to several orders of magnitude over a wide range of tissue thicknesses and absolute values of scatter. Importantly, semiconductor nanocrystal excitation is also often severely constrained to a narrow band very close to the peak emission wavelength (FIG. 4). Hence, under these conditions, the pattern of semiconductor nanocrystal excitation is strikingly similar to that of conventional fluorophores. The emission properties of semiconductor nanocrystals embedded in tissue with wavelength-dependent scatter also differ markedly from non-embedded semiconductor nanocrystals, with a red-shift of peak emission under many conditions.

The results of this study span the extremes of tissue characteristics, from a high Hb to $H_2O$ ratio and wavelength-independent scatter (e.g., blood) to a high $H_2O$ to Hb ratio and wavelength-dependent scatter (e.g., skin). Hence, most tissues will have characteristics between these two extremes. Although the model data suggest that semiconductor nanocrystal excitation and emission wavelengths should be chosen based on the specific tissue(s) being imaged, the data also suggest that Band 3 semiconductor nanocrystals may provide the best overall performance for most biomedical applications. When compared to 840 nm semiconductor nanocrystals, 1320 nm semiconductor nanocrystals are predicted to provide a large improvement in photon yield in tissues such as blood. This result is significant since conventional fluorophores presently being used for biomedical imaging and assays typically have emission within Band 1, i.e., the "near-infrared window" as described in Chance, *Ann. N.Y. Acad. Sci.* 838:29–45 (1998), which is incorporated by reference in its entirety. For example, Cy7, IRDye78, and indocyanine green emit in the 700 nm to 830 nm range. The results suggest that Band 3 semiconductor nanocrystals may greatly outperform Band 1 semiconductor nanocrystals and conventional fluorophores in many tissues. These improvements may be even more pronounced when considering the typically higher QY of NIR and IR semiconductor nanocrystals over conventional fluorophores and their possible insensitivity to photobleaching. The emission curves for Band 3 semiconductor nanocrystals also fall completely within the sensitivity curve of commercially available indium-gallium-arsenide (InGaAs) cameras, making such imaging practical.

It should be noted that the conclusions of this study are not significantly affected by model geometry. When the simulations were run using an analytical solution to the diffusion equation that utilizes a point light source, rather than uniform irradiance (as described, for example, in Fridolin et al., *Phys. Med. Biol.* 45:3779–3792 (2000), which is incorporated by reference in its entirety), similar results were obtained. The conclusions also appear to remain valid when single wavelength excitation, rather than broadband excitation, is used. For example, 1320 nm semiconductor nanocrystals are predicted to retain over 65% of their higher photon yield compared to 840 nm semiconductor nanocrystals when both are excited at their respective first excitation peak.

To simplify the above analysis, the shape of the semiconductor nanocrystal absorbance curves, extinction coefficient at the first absorbance peak, and QY were held constant among the various NIR and IR semiconductor nanocrystals. Of course, the choice of semiconductor material will greatly impact the semiconductor nanocrystal absorbance curve, emission wavelength, particle size, and QY. See, for example, Kershaw et al., *IEEE Journal of Selected Topics in Quantum Electronics* 6, 534–543 (2000), which is incorporated by reference in its entirety. The shape of the absorbance curve, in particular, will be a strong function of the materials used, and even of the purity of the particular semiconductor nanocrystal preparation. The shape difference between materials such as CdSe (see, for example, Leatherdale et al., *J. Phys. Chem. B.* 106, 7619–7622 (2002), which is incorporated by reference in its entirety), CdTe (see, for example, Gaponik et al., *J. of Phys. Chem. B* 106:7177–7185 (2002), which is incorporated by reference in its entirety), and PbSe (see, for example, Chen et al., *Mat. Res. Soc. Symp. Proc.* 691:359–364 (2002), which is incorporated by reference in its entirety) had little overall effect when other variables were held constant, and the spreadsheet format of the model made comparative simulation of semiconductor nanocrystal materials straightforward. It should be emphasized that the predictions of the study can be tested immediately. The literature already provides semiconductor material choices and synthetic strategies for semiconductor nanocrystals emitting within Band 1 (CdTe (see, Gaponik et al., *J. of Phys. Chem. B* 106:7177–7185 (2002) and Murray et al., *J. Am. Chem. Soc.* 115:8706–8715 (1993), each of which is incorporated by reference in its entirety) and InP (see, for example, Bruchez et al., *Science* 281, 2013–2016 (1998)), Band 2 (InAs (Guzelian et al., *Applied Physics Letters* 69:1432–1434 (1996); and Cao and Banin, *J. Am. Chem. Soc.* 122:9692–9702 (2000)), Band 3 (HgTe (Rogach et al., *Advanced Materials* (Weinheim, Germany) 11:552–555 (1999); and Harrison et al., *Materials Science & Engineering, B: Solid-State Materials for Advanced Technology* B69–70:355–360 (2000), each of which is incorporated by reference in its entirety) and PbSe (Chen et al., *Mater. Res. Soc. Symp. Proc.* 691:359–364 (2002), which is incorporated by reference in its entirety) and Band 4 (HgTe (Rogach et al., *Advanced Materials* (Weinheim, Germany) 11:552–555 (1999); and Harrison et al., *Materials Science & Engineering, B: Solid-State Materials for Advanced Technology* B69–70:355–360 (2000), which is incorporated by reference in its entirety) and PbSe (Chen et al., *Mat. Res. Soc. Symp. Proc.* 691:359–364 (2002)).

Simulation can permit semiconductor nanocrystal emission wavelengths to be chosen rationally, before the laborious process of semiconductor nanocrystal production is initiated. Although the absorption advantage of semiconductor nanocrystals can be lost once embedded in certain biological tissue, the tunability of semiconductor nanocrystals to optimal wavelengths remains a feature of paramount importance, and is predicted to result in significant improvements in photon yield over the conventional fluorophores now being used.

Of course, even after choice of optimal excitation and emission wavelengths, it remains to be seen how surface coating, QY, in vivo chemical stability, in vivo photostability, toxicity, and pharmacokinetics will impact the use of semiconductor nanocrystals as contrast agents for biomedical applications. To date, there are no published reports on the toxicity of semiconductor nanocrystals after in vivo administration, and many of the semiconductor materials cited above are known toxins when free in solution. Their toxicity when complexed as nanocrystals remains to be determined. The oligomeric phosphines used for capping in this study appear to have preserved photostability, at least after initial contact with plasma. Clearly the surface coating of semiconductor nanocrystals is of paramount importance with respect to imparting aqueous solubility, minimizing non-specific tissue interactions, and maximizing quantum yield.

Figure 7:
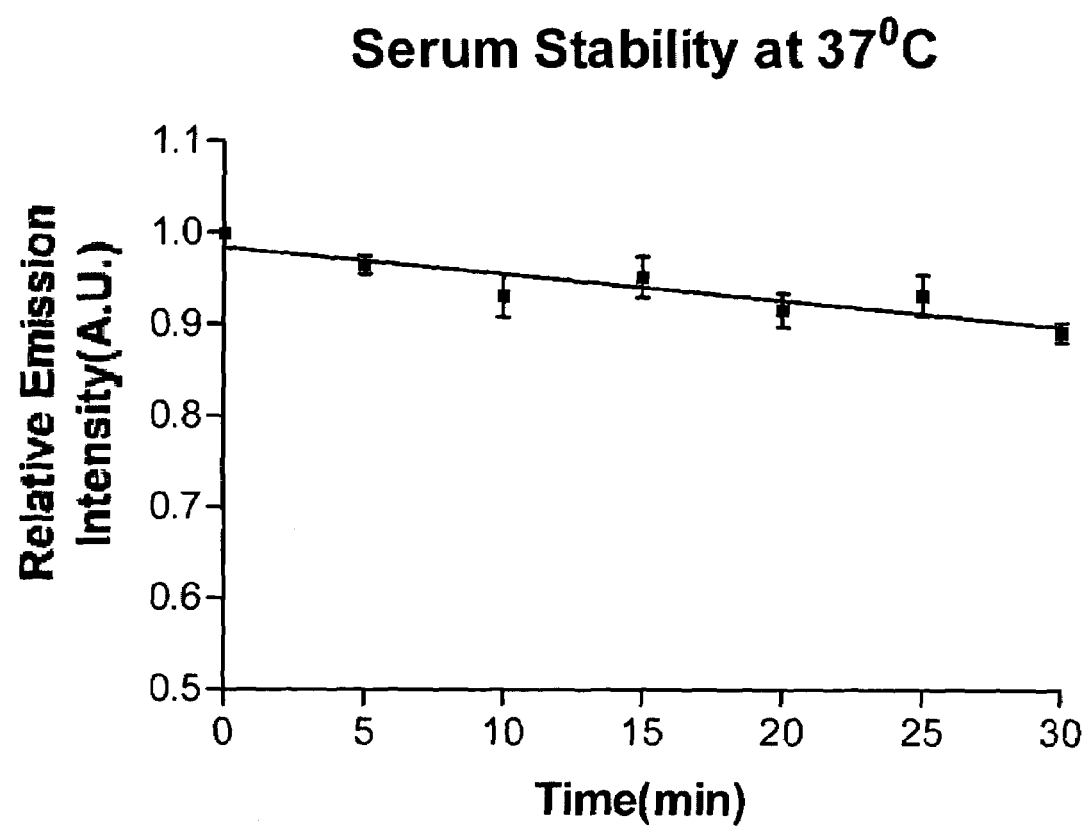
FIG. 7 is a graph depicting serum stability of OPCA-coated NIR nanocrystals at 1 µM incubated in 100% fetal bovine serum at 37° C. for the time indicated.

Referring to FIG. 7, serum stability of OPCA-coated NIR emissive nanocrystals was determined. NIR nanocrystals at 1 μM were incubated in 100% fetal bovine serum at 37° C. for the time indicated in the graph. The NIR emission was measured. Each measurement was made in triplicate, and shown are the mean ±SEM. The nanocrystals were stable in the serum. The OPCA coating rendered NIR nanocrystals stable at 37° C., in 100% serum, for at least 30 min. Since most SLN mapping was performed within the first 15 min, this stability should be more than adequate to accomplish the surgical task.

Figure 8:
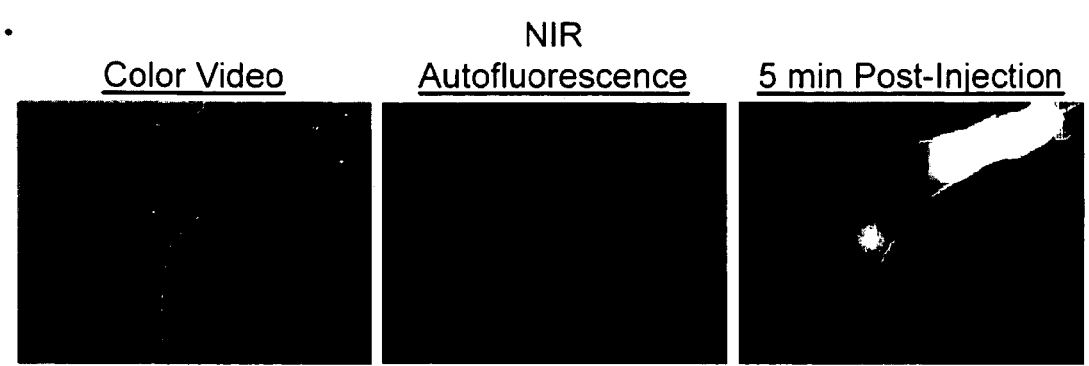
FIG. 8 is a photograph depicting sentinel lymph node mapping using NIR emissive nanocrystals.
Figure 8:
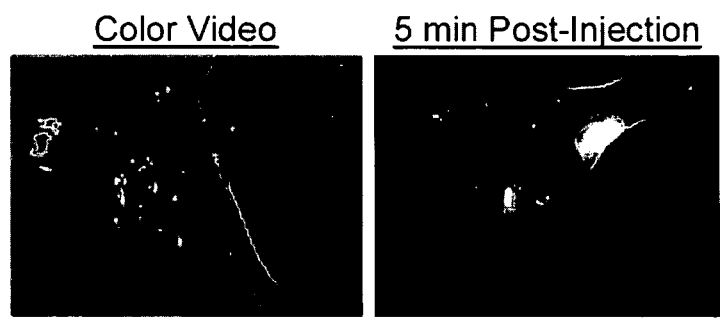

Referring to FIG. 8, the sentinel lymph node in the axilla of a mouse was imaged after sub-dermal injection of NIR nanocrystals (A) and the conventional isosulfan blue due (B) into the left arm. The sentinel lymph node in the axilla of a mouse was imaged after sub-dermal injection of NIR nanocrystals (A) and the conventional isosulfan blue due (B) into the left arm. Within 5 min after injection, the sentinel lymph node was easily detected by monitoring NIR emission from the nanocrystals. The blue dye alone required surgical exploration to find the lymph node, but confirms that the NIR fluorescent object from (A) was the sentinel node. Within 5 min after injection, the sentinel lymph node was easily detected by monitoring NIR emission from the nanocrystals. The blue dye required surgical exploration to find the lymph node, but confirmed that the NIR fluorescent object from (A) was the sentinel node.

From a clinical standpoint, SLN mapping and dissection have revolutionized the assessment of nodal status, particularly for melanoma and breast cancer, cancers for which fairly well-recognized lymphatic patterns of spread are known. Due to technical limitations imposed by radiotracers and vital blue dyes, cancers arising in skin, for example, squamous cell carcinoma, Merkel cell carcinoma, and melanoma, are much more amenable, at present, to SLN mapping and dissection than are visceral cancers such as pancreatic cancer or colorectal cancer. SLN mapping can be performed using NIR nanocrystals and an intraoperative NIR emission imaging system.

Figure 9:
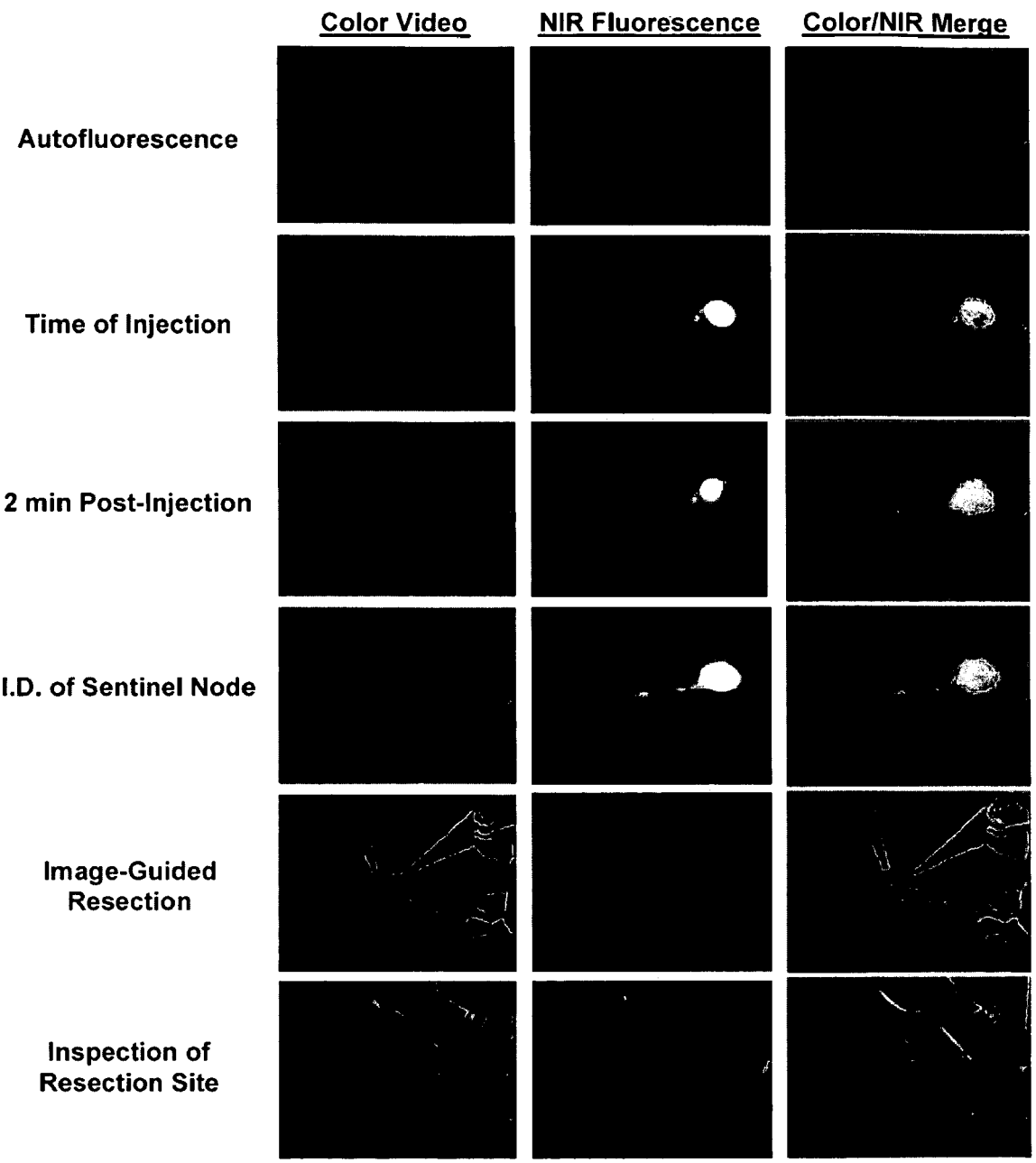
FIG. 9 is a photograph depicting intraoperative sentinel lymph node mapping in a pig using NIR emissive nanocrystals.
Figure 10:
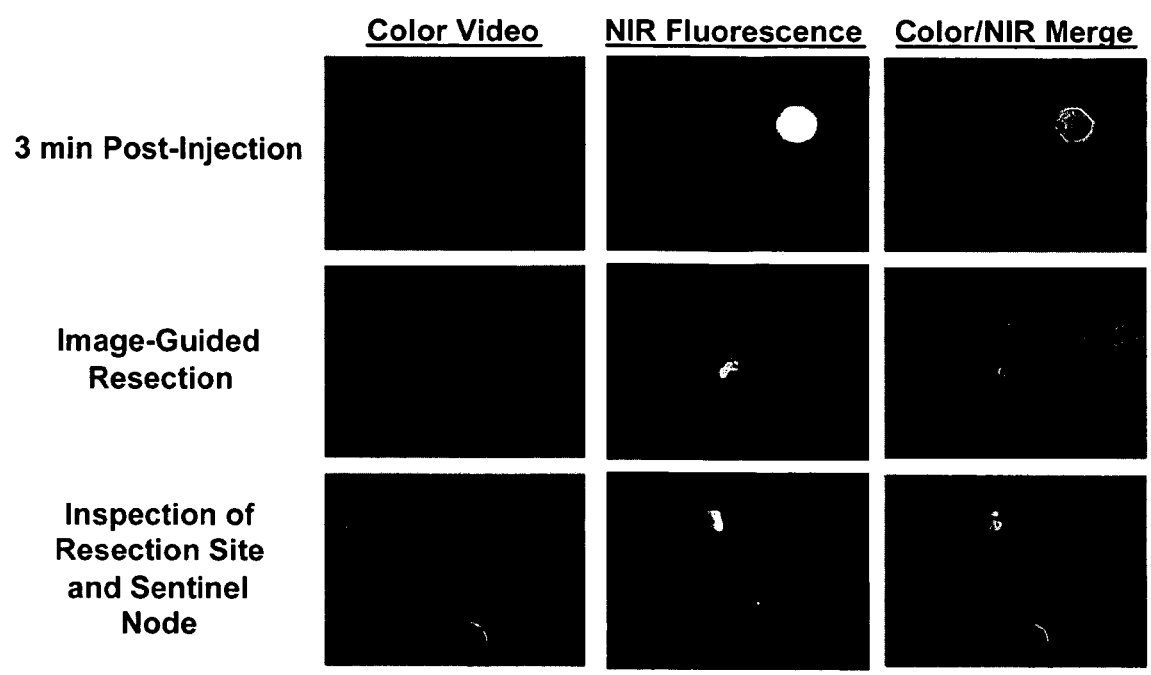
FIG. 10 is a photograph depicting intraoperative sentinel lymph node mapping in a pig using NIR emissive nanocrystals.

The nanocrystals were formulated into an injectable composition having a concentration of nanocrystals of 1–2 micromolar. In experiments involving 30.5 kg pigs, 300 microliters of a 1 micromolar solution of nanocrystals (FIG. 9) or 200 microliters of a 2 micromolar solution of nanocrystals were injected subdermally. After subdermal injection, the 15–20 nm diameter NIR nanocrystals rapidly enter the lymphatics and provide the surgeon with real-time visualization of lymphatic flow and location of the sentinel node in both small and large animals (FIGS. 8–10). In FIG. 9, simulating an actual human case, a pig was injected subdermally with NIR emissive nanocrystals. Using a NIR imaging system, a surgeon can able to map lymph node drainage from the injection site to the sentinel lymph node, including visualization of all lymph channels. The imaging system was then used to direct the surgeon to the site of the sentinel lymph node, permits image-guided resection of the node, and permit confirmation that the entire node was resected. The results in pigs are significant since the sentinel lymph nodes detected are greater than 1 cm below the surface of the skin. Most importantly, in conjunction with the three NIR fluorescence intraoperative imaging systems, the surgeon is able to perform lymph node resection under image guidance (FIGS. 9 and 10) and is able to assess the surgical site for completeness of resection. NIR nanocrystals can be used effectively for sentinel lymph node mapping. The data indicate that NIR light can replace radioactive and chromophoric tracers for this procedure. In particular, in FIG. 9, simulating an actual human case, a pig was injected subdermally with NIR fluorescent nanocrystals. Using a NIR fluorescence imaging system, the surgeon is able to map lymph node drainage from the injection site to the sentinel lymph node, including visualization of all lymph channels. The imaging system is then used to direct the surgeon to the site of the sentinel lymph node, permits image-guided resection of the node, and permit confirmation that the entire node was resected. In FIG. 10, the experiment described in FIG. 9 was repeated using a different pig. This time a non-sentinel lymph node in the same nodal chain can be seen in the color video image and demonstrates the high sensitivity and specificity of the NIR fluorescence imaging system.

Other embodiments are within the scope of the following claims.

What is claimed is:

1. A method of imaging a lymphatic system of an animal comprising:
   introducing at an injection site a composition subcutaneously in the animal, the composition including a particle including a semiconductor nanocrystal;
   exciting the particle with an excitation light source; and
   detecting emission from the particle.

2. The method of claim 1, wherein the composition is introduced proximate to a tumor site in the animal.

3. The method of claim 1, wherein detecting emission includes generating an image in the near-infrared or infrared wavelength region.

4. The method of claim 3, further comprising generating a composite image including a real-time image of an area surrounding the injection site and the image in the near-infrared or infrared wavelength region.

5. The method of claim 4, wherein the particle has a diameter of between 10 nm and 20 nm.

6. The method of claim 1, wherein the particle has a diameter of between 10 nm and 20 nm.

7. The method of claim 2, wherein exciting the particle with an excitation light source includes exposing the animal to white light.

8. The method of claim 1, wherein the particle emits light having a wavelength greater than 800 nm.

9. The method of claim 1, wherein the nanocrystal includes a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating.

10. The method of claim 1, wherein detecting emission includes monitoring a site of the animal that is protected by skin.

11. The method of claim 1, wherein the semiconductor nanocrystal includes a core of a first semiconductor material.

12. The method of claim 11, wherein the first semiconductor material is a Group II-VI compound, a Group II-V compound, a Group III-VI compound, a Group III-V compound, a Group IV-VI compound, a Group I-III-VI compound, a Group II-I V-VI compound, or a Group II-IV-V compound.

13. The method of claim 11, wherein the first semiconductor material is ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

14. The method of claim 11, wherein the semiconductor nanocrystal includes a second semiconductor material overcoated on the first semiconductor material.

15. The method of claim 14, wherein the first semiconductor material has a first band gap, and the second semiconductor material has a second band gap that is larger than the first band gap.

16. The method of claim 14, wherein the second semiconductor material is a Group II-VI compound, a Group II-V compound, a Group III-VI compound, a Group III-V compound, a Group IV-VI compound, a Group I-III-VI compound, a Group II-IV-VI compound, or a Group II-IV-V compound.

17. The method of claim 14, wherein the second semiconductor material is ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

18. The method of claim 17, wherein the first semiconductor material and the second semiconductor material are selected so that, upon excitation, one carrier is substantially confined to the core and the other carrier is substantially confined to the overcoating.

19. The method of claim 1, wherein the semiconductor nanocrystal includes an outer layer including a polydentate ligand.

20. A method of imaging a lymphatic system of an animal comprising:
   introducing at an injection site a composition subcutaneously in the animal, the composition including a particle including a semiconductor nanocrystal, wherein the nanocrystal includes a core of a first semiconductor material and an overcoating of a second semiconductor material on the core wherein the first semiconductor material and the second semiconductor material are selected so that, upon excitation, one carrier is substantially confined to the core and the other carrier is substantially confined to the overcoating;
   exciting the particle with an excitation light source;
   detecting emission from the particle; and
   generating a real-time image of an area surrounding the injection site.

21. The method of claim 20, wherein generating the real-time image includes generating an image in the near-infrared or infrared wavelength region.

22. The method of claim 20, wherein generating the real-time image includes generating an image in the visible wavelength region.

23. The method of claim 20, wherein generating the real-time image includes generating a composite image including an image in the visible wavelength region and an image in the near-infrared or infrared wavelength region.

24. The method of claim 20, wherein the excitation light source is a broadband white light source.

* * * * *